US012398405B2

(12) United States Patent
Erfle et al.

(10) Patent No.: US 12,398,405 B2
(45) Date of Patent: Aug. 26, 2025

(54) BIOACTIVE COMPOUND DELIVERY ASSEMBLY

(71) Applicants: UNIVERSITÄT HEIDELBERG, Heidelberg (DE); STATE RESEARCH INSTITUTE CENTER FOR PHYSICAL SCIENCES AND TECHNOLOGY, Vilnius (LT)

(72) Inventors: Holger Erfle, Neckarsteinach (DE); Ramunas Valiokas, Trakai (LT); Vytautas Cepla, Vilnius (LT); Vytaute Starkuviene, Neckarsteinach (DE)

(73) Assignees: Universitat Heidelberg, Heidelberg (DE); State Research Institute Center for Physical Sciences and Technology, Vilnius (LT)

( * ) Notice: Subject to any disclaimer, the term of this patent is extended or adjusted under 35 U.S.C. 154(b) by 1733 days.

(21) Appl. No.: 15/998,902

(22) PCT Filed: Feb. 16, 2017

(86) PCT No.: PCT/EP2017/000226
§ 371 (c)(1),
(2) Date: Aug. 16, 2018

(87) PCT Pub. No.: WO2017/140429
PCT Pub. Date: Aug. 24, 2017

(65) Prior Publication Data
US 2021/0207172 A1    Jul. 8, 2021

(30) Foreign Application Priority Data
Feb. 17, 2016 (EP) .................... 16000400

(51) Int. Cl.
*C12N 15/88* (2006.01)
*A61L 27/34* (2006.01)
*A61L 29/08* (2006.01)

(52) U.S. Cl.
CPC .............. *C12N 15/88* (2013.01); *A61L 27/34* (2013.01); *A61L 29/085* (2013.01)

(58) Field of Classification Search
CPC .......... C12N 15/88; A61K 9/14; A61K 47/48; A61F 2/06; A61L 33/00; B01J 19/00; C08L 89/00
See application file for complete search history.

(56) References Cited

U.S. PATENT DOCUMENTS 5,776,748 A      7/1998  Singhvi et al.
2002/0055731 A1*  5/2002  Atala ................. A61K 41/0047
                                                604/20

(Continued)

OTHER PUBLICATIONS

International Search Report and Written Opinion for International Application No. PCT/EP/2017/000226 mailed Feb. 16, 2017.

(Continued)

*Primary Examiner* — Dah-Wei D. Yuan
*Assistant Examiner* — Andrew J Bowman
(74) *Attorney, Agent, or Firm* — Foley Hoag LLP; David P. Halstead; Mohanad Mossalam

(57) ABSTRACT

The present invention relates to a bioactive compound delivery assembly, a method for stabilization and/or encapsulation of bioactive compound compositions, a method for solid-supported transfection of living cells as well as a use of the bioactive compound delivery assembly.

13 Claims, 15 Drawing Sheets

(56) References Cited

U.S. PATENT DOCUMENTS

Figure 1:
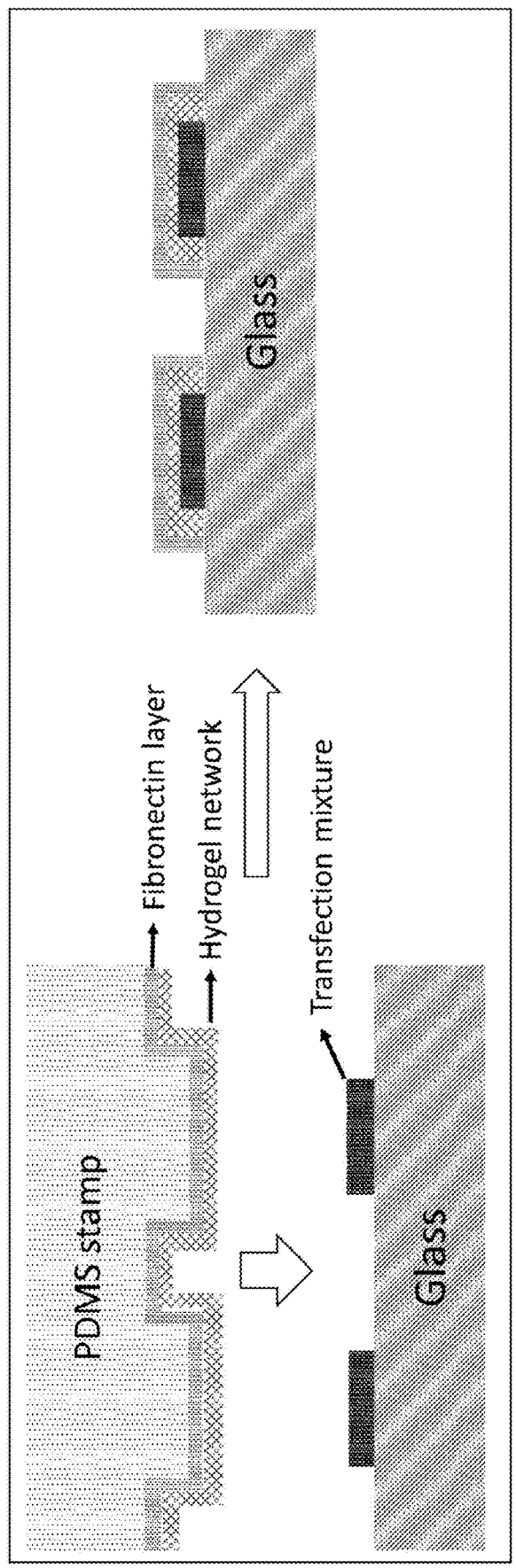

| | | | |
|---|---|---|---|
| 2003/0059537 A1 | 3/2003 | Chilkoti et al. | |
| 2004/0106987 A1* | 6/2004 | Palasis | A61F 2/91 623/1.42 |
| 2007/0110888 A1* | 5/2007 | Radhakrishnan | B41M 3/006 427/256 |
| 2009/0263430 A1* | 10/2009 | Scheibel | C08L 89/00 428/478.2 |
| 2011/0111031 A1* | 5/2011 | Jiang | A61K 9/0024 514/327 |

OTHER PUBLICATIONS

Wang et al., Nanolayer Biomaterial Coatings of Silk Fibroin for Controlled Release, J. Controlled Release, 23 pages, Jun. 14, 2007, https://www.ncbi.nlm.nih.gov/pmc/articles/PMC695962/pdf/nihms29668.pdf.†

Kapoor et al. Silk Protein-Based Hydrogels: Promising Advanced Material for Biomedical Applications, Acta Biomaterialia 31 (2016) 17-32.†

Hardy et al., Polymeric Materials Based on Silk Proteins, Polymer 49 (2008) 4309-4327.†

\* cited by examiner
† cited by third party

BIOACTIVE COMPOUND DELIVERY ASSEMBLY

RELATED APPLICATIONS

This patent application is a national-stage application of International Application PCT/EP2017/000226, filed on Feb. 16, 2017, which claims priority to application Ser. No. 16/000,400.8, filed on Feb. 17, 2016 in European Patent Office.

The present invention relates to a bioactive compound delivery assembly, a method for stabilization and/or encapsulation of bioactive compound compositions, a method for solid-supported transfection of living cells as well as a use of the bioactive compound delivery assembly.

In the state of the art, enclosure of bioactive substances is achieved by protective layers synthesized in situ or in bulk by employing different polymerization, microencapsulation, or lipid assembly techniques. However, with said methods it was so far not possible to dose, array and/or pattern substances on a support and then enclosing them. A further drawback of the previously known methods represents the imprecise deposition of the protective layer, especially in the context of rapidly developing medical and biotechnologies based on miniaturization. In view of said drawbacks, the enclosure of important bioactive substances, as e.g. small interfering RNA (siRNA), has not been seriously approached. Thus, siRNA screening technologies did so far not employ any protection layers at all. In that case, transfection of cells started immediately as soon as the cells were applied to microwells containing dispensed and dried transfection mixtures. In consequence, a controlled delivery of bioactive substances, as e.g. transfection mixtures, to cells as well as a functional modification of the surfaces of implants, prosthesis, medical devices, and drug delivery tools, especially via deposition of microscopic assemblies of bioactive substances, was so far not possible.

Thus, the technical problem underlying the present invention is to provide means for the temporally and spatially controlled delivery of bioactive substances, as e.g. transfection mixtures, to cells and for the functional modification of the surfaces of implants, prostheses, medical devices, and drug delivery tools.

The solution to the above technical problem is achieved by the embodiments characterized in the claims.

In particular, in a first aspect, the present invention relates to a bioactive compound delivery assembly, comprising a (physical) support, at least one bioactive compound composition disposed on the support, and at least one stabilization/protection layer partially or fully covering the at least one bioactive compound composition, wherein the stabilization layer comprises a protein- and/or peptide-polymer hydrogel (hereafter referred to as the peptide-polymer hydrogel).

The term "peptide-polymer hydrogel" as used herein relates to a peptide-polymer hydrogel as well as a protein-polymer hydrogel. Likewise, the term "peptide-PEG hydrogel" as used herein relates to a peptide-PEG hydrogel as well as a protein-PEG hydrogel.

The term "bioactive compound delivery assembly" relates to an assembly, which is capable of providing a bioactive compound in a stabilized and/or an encapsulated form.

The term "support" as used herein does not have any specific limitations, and relates, for example, to at least one member selected from the group consisting of glass, semiconductor, metal, silicon, polymer-substrate, polymer coating, bioplastics, elastomers, ceramics, living tissue, as e.g. skin, implant, prosthesis, medical devices, and insoluble polymer material, which can be an organic polymer, such as a polyamide, a vinyl polymer (e.g. poly(meth)acrylate, polystyrene and polyvinyl alcohol, or derivatives thereof), or a hydrogel, a natural polymer such as cellulose, dextrane, agarose, chitin and polyamino acids, an assembly or conjugate of synthetic peptides, collagen hydrogels, or an inorganic polymer, such as glass or metallohydroxide. The surface of the support can be geometrically flat, curved, and corrugated, and may contain different microscopic and/or macroscopic topographies, protruding and intruding features, pits, channels, pores, etc. The support can be in the form of a microcarrier, particles, membranes, strips, paper, film, or plates, such as microtiter plates or microarrays, as well as medical devices, as e.g. contact lenses, catheters, and electrodes, implants, and prosthesis (or constituent parts of these). The term "microarray" as used herein may mean any arrangement of the material spots in addressable locations on the support in periodic or gradient or any other patterns. The surface of the microarray may be structured and may have features shaped like discs, lines, triangles, rectangles and any other geometrical shapes, which consist of synthetic compounds, polymers, proteins, peptides, lipids, bioactive substances, biocompatible or antifouling materials, deposited as single or multiple layers, resulting in a so-called "biochip" device. Preferably, the support is at least one member selected from the group consisting of glass, semiconductor, insoluble polymer material, medical device, implant, and prosthesis.

The term "implant" as used herein does not have any specific limitations, and relates, for example, to plates, pins, screws, membranes, tubes, pacemaker devices, skin or corneal substitutes, any other devices made from metal, plastic, ceramic or other natural or artificial materials, as well as from skin, bone or other body tissues. The implant is intended for temporal or permanent insertion into a human or other mammal body.

The term "prosthesis" as used herein does not have any specific limitations, and denotes an implant that is introduced into a human or other mammal body to replace a removed or dysfunctional body part, organ, or tissue.

The support may be coated or uncoated. Preferably, the support is a support being, for example coated with/chemically attached to at least one member selected from collagen, fibronectin, laminin, peptides, lipids, Gamma Amino Propyl Silane (GAPS), other silanes, mono- or multifunctional organic compounds, sucrose, polyethylene glycol, polyethylene glycol based hydrogels, as e.g. polyethylene glycol acrylate hydrogel and polyethylene glycol methacrylate (PEG MA) hydrogel, poly-lysine, hyaluronic acid, Matrigel or any other natural or synthetic hydrogel. In the above context, polyethylene glycol as well as the polyethylene glycol subunit of the polyethylene glycol based hydrogels may be substituted or unsubstituted. Possible substituents are selected from the group consisting of amino groups, epoxy groups, carboxy groups, maleimide groups, thiol groups, alkyl groups, alkenyl groups, alkynyl groups, azide groups, imido groups, and ester groups, as e.g. activated carboxy esters groups. Preferably, the support is coated with a polyethylene glycol-based hydrogel, more preferably a polyethylene glycol methacrylate (PEG MA) hydrogel. More preferably the support is coated with a biocompatible polyethylene glycol-based hydrogel, even more preferably with a biocompatible PEG MA hydrogel. By coating the support with a biocompatible PEG MA hydrogel an improved control of the surface properties is advantageously possible and improved selectivity of the cell-adhesiveness can be imparted on the support. Preferably, the polyethylene glycol methacrylate (PEG MA) is synthesized from hydroxyethyl methacrylate (HEMA), polyethylene glycol methacrylate (PEGMA) and methacrylic acid (MAA).

In the context of the present invention, the terms "biocompatible" and "biocompatibility" denote the ability of an entity to be in contact with a living system, organs, tissues, body fluids, proteins and other biomolecules/biomolecular solutions without producing an adverse effect and/or non-specific or uncontrolled binding.

According to the present invention, the terms "spot" and "pattern" refer to an area on the surface of the support. The spot or pattern may comprise reagents and/or layers which may be brought/produced on the surface of the support by various methods, including deposition with a needle/pin, microcontact printing, ink-jet printing, aerosol jet printing, photolithography, electron beam lithography, scanning probe nanolithography, laser writing, or other patterning techniques. Preferably, the reagents and/or layers are brought at the spot/pattern by pin arraying and microcontact printing.

According to the present invention, at least one bioactive compound composition is disposed/spotted on the support and at least one stabilization layer partially of fully covers the at least one bioactive compound composition.

The term "bioactive compound composition" as used herein is not specifically limited as long as the composition comprises at least one bioactive compound. For example, the bioactive compound composition may comprise transfection mixtures, growth factors, proteins, antibodies, peptides, anti-inflammatory substances, antibiotics, signaling molecules, chemokines, and/or antiviral drugs. Preferably, the bioactive compound composition consists of a transfection mixture.

Transfection mixtures according to the present invention are not particularly limited and are known in the art. For example, the transfection mixture may comprise a transfection reagent, at least one protein and/or at least one nucleic acid molecule. Preferably, the transfection mixture comprises a transfection reagent and at least one nucleic acid molecule. More preferably, the transfection mixture consists of a transfection reagent and at least one nucleic acid molecule.

The transfection reagent may be any commercially available transfection agent which is suitable for transfecting proteins and/or nucleic acids into cells. The term "transfection agent" is not limited to agents which are suitable for transfecting proteins and/or nucleic acid molecules into cells, but also comprises agents which are suitable to transfect other molecules into cells, like for example DNA, RNA, siRNA, proteins or antibodies. Any transfection agent, which does not prevent the transfection of proteins and/or nucleic acid molecules into cells, is a transfection agent according to the term "transfection agent" as used herein. Preferably, the transfection agent is selected from the group consisting of Novagen ProteoJuice, OZ Biosciences DreamFect Gold, ibidi Torpedo DNA, Peqlab PeqFect siRNA, Invitrogen Lipofectamine 2000, Invitrogen Lipofectamine 3000, Invitrogen Lipofectamine RNAiMAX and Gelantis GeneSilencer.

The term "protein" used herein does not underlie a specific restriction and may include any protein, protein complex or polypeptide, including recombinant proteins, protein complexes and polypeptides either isolated from a natural source or obtained via recombinant DNA technology or chemical synthesis, or a biologically active derivative thereof.

As used herein, the term "biologically active derivative of a protein" includes any derivative of a protein, protein complex or polypeptide having substantially or partially the same functional and/or biological properties of the native protein such as binding properties, and/or the same structural basis, such as a peptidic backbone. The oligo- or polypeptide sequences of the functionally active derivatives, which may be reduced (short) sequences of the natural polypeptide (protein) such as RGD, may contain deletions, additions and/or substitution of amino acids whose absence, presence and/or substitution, respectively, do not have any substantial negative impact on the activity of the polypeptide, e.g. amino acids which are located in a part of the polypeptide sequence that does not contribute to the biological activity of the protein. Minor deletions, additions and/or substitutions of amino acids of the respective polypeptide sequences which are not altering the biological activity of said polypeptide are also included in the present application as biologically active derivatives. Moreover, a biologically active derivative of a protein may not only be a short sequence of the corresponding protein, protein complex or polypeptide, but also a mimetic peptide that mimics the natural function of the protein, protein complex or polypeptide, a self-assembling peptide that is designed to form two- and three-dimensional structures, aggregates, a crosslinked peptide, or a pharmaceutical peptide (acting as pharmaceutical substance or an ingredient thereof). The biologically active derivative of a protein may be produced by chemical synthesis or biotechnologically.

A protein obtained from a natural source may be any protein isolated from a natural source, like for example a body fluid derived from a mammal. In a preferred embodiment, the mammal is selected from the group consisting of mouse, human, rat, cat, dog, and monkey.

The protein may be produced by any method known in the art. This may include any method known in the art for the production of recombinant DNA by genetic engineering, e.g. via reverse transcription of RNA and/or amplification of DNA. This includes methods, which comprise the recombinant production of the protein.

The recombinant protein used may be produced by any method known in the art. This may include any method known in the art for (i) the production of recombinant DNA by genetic engineering, e.g. via reverse transcription of RNA and/or amplification of DNA, (ii) the introduction of recombinant DNA into prokaryotic or eukaryotic cells by transfection, e.g. via electroporation or microinjection, (iii) the cultivation of said transformed cells, e.g. in a continuous or batch-wise manner, (iv) the expression of the protein, e.g. constitutive or upon induction, and (v) the isolation of the protein, e.g. from the culture medium or by harvesting the transformed cells, in order to (vi) obtain purified recombinant protein, e.g. via anion exchange chromatography or affinity chromatography.

For example, the recombinant DNA coding for the protein, e.g. a plasmid, may also contain a DNA sequence encoding a selectable marker for selecting the cells which have been successfully transfected with the plasmid. In one example, the plasmid may also confer resistance to a selectable marker, e.g. to the antibiotic drug G418, by delivering a resistance gene, e.g. the neo resistance gene conferring resistance to G418.

The production of the protein may include any method known in the art for the introduction of recombinant DNA into cells, which might be mammalian cells, bacterial cells or insect cells, by transfection, e.g. via electroporation or microinjection. For example, the recombinant expression of the protein can be achieved by introducing an expression plasmid containing the protein encoding DNA sequence under the control of one or more regulating sequences such as a strong promoter, into a suitable host cell line by an appropriate transfection method resulting in cells having the introduced sequences stably integrated into the genome. The calcium-phosphate co-precipitation method is an example of a transfection method.

The production of the protein may also include any method known in the art for the cultivation of said transformed cells, e.g. in a continuous or batch-wise manner, and the expression of the protein e.g. constitutive or upon induction. In one specific example the nucleic acid coding for the protein contained in a host organism is expressed via an expression mode selected from the group consisting of induced, transient, and permanent expression. Any expression system known in the art or commercially available can be employed for the expression of a recombinant nucleic acid encoding the protein, including the use of regulatory systems such as suitable, e.g. controllable promoters, enhancers etc.

The production of the protein may also include any method known in the art for the isolation of the protein, e.g. from the culture medium or by harvesting the transformed cells. For example, the protein-producing cells can be identified by isolating single-cell derived populations i.e. cell clones, via dilution after transfection and optionally via addition of a selective drug to the medium. After isolation the identified cell clones may be cultivated until confluency in order to enable the measurement of the protein content of the cell culture supernatant by enzyme-linked immunosorbent assay (ELISA) technique.

Additionally, the production of the protein may include any method known in the art for the purification of the protein, e.g. via anion exchange chromatography or affinity chromatography. In one preferred embodiment the protein can be purified from cell culture supernatants by semi-affinity calcium-dependent anion exchange chromatography, e.g. in an endotoxin-free system. The purified protein may be analyzed by methods known in the art for analyzing recombinant proteins, e.g. the ELISA technique, mass spectrometry, and surface plasmon resonance. In addition, the protein integrity and activity may be assessed. It is within the knowledge of a person skilled in the art to choose the optimal parameters, such as buffer system, temperature and pH for the respective detection system to be used.

In one specific example, the protein transfected into a cell is expressed in a host cell type with the ability to perform posttranslational modifications. The ability to perform posttranslational modifications of the protein expressing host cell lines may be for example analyzed by mass spectrometric analysis.

The host cell type used for the recombinant production of the protein may be any bacterial or mammalian cell, preferably with the ability to perform posttranslational modifications of the protein. There is no particular limitation to the media, reagents and conditions used for culturing the cells in the cell culture used for the recombinant protein production of including culturing the cells in a continuous or batch-wise manner. The desired protein which has been expressed by the cells and which, dependent on the transfection/vector-system used, is contained in the cells or secreted into the medium for culturing cells, can be isolated/recovered from cell culture using methods known in the art.

In a preferred embodiment the protein is an antibody or a fragment thereof.

The term "antibody" as used herein may be any antibody including biologically active fragments of an antibody having substantially the same biological function as the antibody, e.g. the ability to bind a specific antigen. In particular, the antibody can be selected from the group consisting of a naturally occurring antibody, a polyclonal antibody, a chimeric antibody, a monoclonal antibody, e.g. derived by conventional hybridoma techniques, and an antibody or antibody fragment obtained by recombinant techniques, e.g. phage display or ribosome display, mutated antibodies and (semi)-synthetic antibodies. For example, the antibody or at least one fragment thereof may contain one or more mutations or variations, such as added, deleted or substituted amino acids or nucleic acids, as long as it has no negative effect on the interaction with the specific antigen. The antibody may belong to any immunoglobulin class.

The term "fragment" used herein means any portion of an antibody as defined above as long as it has the ability to bind to the desired antigen. Moreover, a fragment may comprise several different portions from said antigen. Examples of fragments of an antibody are antigen binding fragment (FAB), single chain variable fragment (scFv), variable domain of the heavy chain (VH), variable domain of the light chain (VL), complementary determining regions (CDRs), and combinations thereof. The term "scFv" used herein means a fusion of the variable regions of the heavy and light chains of any immunoglobulin, linked together with a linker, such as for example serine, glycine, any other natural or non-natural amino acid, a peptide, a protein, or a nucleic acid.

For example, the antibody or the at least one fragment thereof may be a humanized antibody or at least one fragment thereof derived from the murine antibody H398. There is no limitation as to the technique of humanization of the antibody, as long as the antibody binds to the desired antigen. Examples of humanization include CDR-grafting, The expression "humanized antibody" used herein means any antibody in which protein engineering is used to reduce the amount of foreign ("non-human") protein sequence by swapping e.g. rodent antibody constant regions and/or the variable-domain framework with sequences that are found in human antibodies. In a further embodiment of the antibody fragment as defined above, the at least one fragment is a Fab-region, a scFv, or any post-translationally processed recombinant derivative thereof.

In another preferred embodiment, the protein is a nuclease being involved in genome editing, like for example CAS9, transcription-like effector (TALEN), or zinc-finger nucleases.

The term "nucleic acid molecule" used herein does not underlie a specific restriction and may include any nucleic acid molecule of any length, including polynucleotides, oligonucleotides, aptamers, deoxyribonucleic acid (DNA), ribonucleic acid (RNA), and artificial nucleic acid analogs, like morpholinos, bridged nucleic acid (BNA), peptide nucleic acid (PNA), locked nucleic acid (LNA), glycol nucleic acid (GNA), and therose nucleic acid (TNA). In a preferred embodiment the at least one nucleic acid molecule is selected from the group consisting of DNA, mRNA, siRNA, miRNA, sgRNA, gRNA, cDNA, DNA aptameres, viral transfection vectors, and morpholino oligomers. Most preferably, the at least one nucleic acid molecule is a siRNA, gRNA aptamere, viral transfection vector, and/or morpholino oligomer.

The siRNA molecule can be any short single or double stranded RNA, preferably of 15 to 30 nucleotides, more preferably of 19 to 25, most preferably of 21 to 23 nucleotides length. The siRNA may contain modifications, including modifications of nucleobases and/or modifications of the backbone, as well as overhangs at the 3' and/or 5' end of the sense and/or antisense strand.

The cDNA molecule can be any cDNA molecule known in the art. Methods for obtaining cDNA by synthesizing DNA using a messenger RNA (mRNA) as a template employing the reverse transcriptase function of a DNA polymerase are known to a person skilled in the art. In a preferred embodiment, the cDNA molecule is a double-stranded DNA molecule having a length form 20 bp to 15000 bp, more preferably from 40 bp to 6000 bp, more preferably from 100 bp to 4000 bp.

The term nucleic acid molecule as used herein includes recombinant and synthetic nucleic acid molecules as well as nucleic acid molecules which are isolated from a natural source, including biologically active derivatives thereof.

As used herein, the term "biologically active derivative of a nucleic acid molecule" includes any derivative of a nucleic acid molecule having substantially the same functional and/or biological properties of the at least one nucleic acid molecule such as coding properties, and/or the same structural basis, such as a nucleotide backbone. The nucleotide sequences of the functionally active derivatives may contain deletions, additions and/or substitution of nucleotides whose absence, presence and/or substitution, respectively, do not have any substantial negative impact on the activity of the nucleic acid molecule, e.g. nucleotides which are located in a part of the nucleotide sequence that does not contribute to the biological activity of the nucleic acid molecule. Minor deletions, additions and/or substitutions of nucleotides of the respective nucleotide sequences which are not altering the biological activity of said nucleic acid molecule are also included in the present application as biologically active derivatives.

A nucleic acid molecule obtained from a natural source may be any nucleic acid molecule isolated from a natural source, like for example a tissue or cell sample derived from a mammal. In a preferred embodiment, the mammal is selected from the group consisting of mouse, human, rat, cat, dog, and monkey.

The nucleic acid molecule may be produced by any method known in the art. This may include any method known in the art for the production of recombinant DNA by genetic engineering, e.g. via reverse transcription of RNA and/or amplification of DNA. This includes methods which comprise the recombinant production of the nucleic acid molecule.

The recombinant nucleic acid molecule used may be produced by any method known in the art. This may include any method known in the art for (i) the production of recombinant DNA by genetic engineering, e.g. via reverse transcription of RNA and/or amplification of DNA, (ii) the introduction of recombinant DNA into prokaryotic or eukaryotic cells by transfection, e.g. via electroporation or microinjection, (iii) the cultivation of said transformed cells, e.g. in a continuous or batch-wise manner, and (iv) the isolation of the nucleic acid molecule, e.g. by harvesting the transformed cells, in order to (v) obtain purified recombinant nucleic acid molecule, e.g. via anion exchange chromatography or affinity chromatography.

For example, the recombinant nucleic acid molecule, e.g. a plasmid, may also contain a DNA sequence encoding a selectable marker for selecting the cells which have been successfully transfected with the plasmid. In an example, the plasmid may also confer resistance to a selectable marker, e.g. to the antibiotic drug G418, by delivering a resistance gene, e.g. the neo resistance gene conferring resistance to G418.

The production of the nucleic acid molecule may include any method known in the art for the introduction of recombinant DNA into cells, which might be mammalian cells, bacterial cells or insect cells, by transfection, e.g. via electroporation or microinjection. The production of the nucleic acid molecule may also include any method known in the art for the cultivation of said transformed cells, e.g. in a continuous or batch-wise manner The production of the nucleic acid molecule may also include any method known in the art for the isolation of cells containing the nucleic acid molecule, e.g. from the culture medium or by harvesting the transformed cells. For example, the nucleic acid molecule containing cells can be identified by isolating single-cell derived populations i.e. cell clones, via dilution after transfection and optionally via addition of a selective drug to the medium. After isolation the identified cell clones may be cultivated until confluency.

Protocols for recombinant DNA isolation, cloning and sequencing are well known in the art. Further, methods for the production and isolation of RNA molecules are well known in the art.

Within the scope of the invention, the term "cells" means a generic term and encompasses individual cells, tissues, organs, insect cells, avian cells, mammalian cells, bacterial cells, primary cells, cancer cells, continuous cell lines, stem cells and/or genetically engineered cells, such as recombinant cells expressing a heterologous polypeptide or protein and/or containing a recombinant nucleic acid molecule and/or stable expressing cells.

According to the present invention, at least one stabilization layer partially or fully covers the at least one bioactive compound composition disposed over the support. By this means it is advantageously possible to control the delivery of the bioactive compound composition in terms of location and time or to functionally modify the surface of supports, as e.g. implants, prostheses, medical devices, and drug delivery devices/tools. For example, by the bioactive compound delivery assembly according to the present invention it is possible to realize solid-supported transfection, as e.g. siRNA transfection, of living cells in different dish/plate formats and to integrate it in automated screening technologies, as e.g. high-throughput screening (HTS), as well as in individual experimentations. Preferably, the stabilization layer physically stabilizes bioactive compound compositions, which are provided on a support e.g. via printing by a robotic system. By this stabilization the spotted/patterned and covered bioactive compound compositions are not immediately dissolved when transferred into a liquid media. In a preferred embodiment, living cells are able to remove/degrade the stabilization layer upon contacting the spots/patterns, which comprise the bioactive compound composition and the stabilization layer in this order from the surface of the support, within a certain period of time and the cells are staying/moving on the surface of the support and/or the covered spots/patterns.

The term "spotted and covered bioactive compound composition" refers to the part of a bioactive compound composition, which is disposed on a support and which is covered with at least one stabilization layer.

The number of stabilizing layers partially or fully covering a bioactive compound composition is not particularly limited. Thus, a bioactive compound composition can be covered by more than one stabilization layer, wherein the stabilization layers may or may not overlap each other.

Preferably, the stabilization layers do overlap each other at least partially. In a preferred embodiment, by covering the bioactive compound composition by more than one stabilization layer, the bioactive compound composition can be further stabilized. Preferably, when contacting the spotted and covered bioactive compound composition with cells, the time until the cells come into contact with the bioactive compound composition can be increased by increasing the number or the degree of chemical or physical crosslinking of the stabilization layers covering said bioactive compound composition. For example, a bioactive compound composition may be partially or fully covered with 1 to 10 stabilization layers, preferably with 1 to 7 stabilization layers, more preferably 1 to 4 stabilization layers, more preferably 1 or 2 stabilization layers and most preferably 1 stabilization layer.

In a preferred embodiment of the present invention, the bioactive compound delivery assembly comprises at least two bioactive compound compositions disposed on the support with at least one bioactive compound composition not being covered by a stabilization layer and with at least one other bioactive compound composition being fully covered with at least one stabilization layer. Preferably, when disposing at least one further bioactive compound composition, which is not covered by a stabilization layer, besides other fully covered bioactive compound compositions, it is advantageously possible to realize sequential contacting of e.g. cells with the different bioactive compound compositions, as e.g. different transfection mixtures.

The number of bioactive compound compositions being partially or fully covered by the same stabilization layer is not particularly limited. Thus, one stabilization layer can cover more than one bioactive compound composition, wherein the bioactive compound compositions are located at different spots.

Preferably, the thickness of the stabilization layer is in the range of 0.1 to 1000 nm, more preferably 0.1 to 100 nm, more preferably 0.5 to 50 nm, more preferably 1 to 25 nm, more preferably 1 to 15 nm, more preferably 2 to 12 nm, and most preferably 5 to 10 nm. Since the thickness of the stabilization layer according to the present invention preferably lies in the nanometer range, the stabilization layer may represent an ultra-thin stabilization layer and may thus also be referred to as a "nanofoil". Preferably, the thickness of the stabilization layer is selected e.g. in accordance with the "capacity" of the cells to remove the layer within a reasonable time frame, as e.g. 1 h to 30 d, preferably 2 h to 4 d, more preferably 5 h to 2 d, and most preferably 10 h to 24 h.

Preferably, at least one lateral dimension (e.g. the width of a stripe) of the stabilization layer is in the range of 1 to 10000 µm, more preferably 1 to 1000 µm, more preferably 10 to 750 µm, more preferably 50 to 500 µm, more preferably 100 to 300 µm, and most preferably 150 to 250 µm.

Preferably, the lateral dimensions of the stabilization layer are equal to or larger than the spot/pattern comprising the bioactive compound composition, as e.g. a transfection mixture, under it, in order to seal the latter.

Preferably, diffusion of the bioactive compound or bioactive compound composition through the stabilization layer does not occur at all prior a cell adheres and removes the stabilization layer. More preferably, the stabilization layer is impermeable to the bioactive compound or bioactive compound composition.

Preferably, a spot containing the bioactive compound composition disposed on the support has borders, for efficient enveloping by subsequently applying the stabilization layer. The term "border" in this regard refers to a transition zone between a surface region that contains the disposed bioactive compound composition and a surface region that is unmodified (pristine). Ideally, outside a border of a spot containing the bioactive compound composition no bioactive compound (or only traces thereof) can be detected by any known surface analysis technique (e.g. optical microscopy, imaging ellipsometry, scanning electron microscopy, scanning probe microscopy, imaging photoelectron spectroscopy, imaging infrared spectroscopy, mass spectrometry imaging, etc.). The border can be a sharp transition zone (on a scale of 1 Å to 1 µm) or it can be broader, e.g in a form of a gradient. The border can be in one dimension (e.g. when the bioactive compound composition is disposed over the surface in a form of stripe/line patterns) or in two dimensions (the bioactive compound composition is in a form of circular spots, discs, rectangles, etc.). The term "border" in this invention is used to differ from systems, in which the whole surface is coated by a continuous layer of bioactive compound compositions.

Preferably, the spots are microspots, e.g. having dimensions ranging from 1 nm to 1000 µm. In this invention, individual nanoparticles or microparticles (material particles of spherical or asymmetric shapes, comprising bioactive substances and having their radii or at least one other dimension ranging from 1 to 1000 nm) or groups thereof disposed over the surface are also covered by the term "spots". Moreover, the stabilization layer may also be disposed over the bioactive compound compositions as microscopic spots (microspots) or patterns, i.e. it also may have borders. If needed, the bioactive compound containing microspots and the stabilization layer microspots can be aligned to partially or fully overlap, i.e. to perfectly match each other's position. Preferably, the microspots of bioactive compound composition are used to dose the bioactive compound in such doses, that the bioactive compound composition can be efficiently covered and sealed by the ultrathin stabilization layer (that is preferably applied as a nanofoil). In a preferred embodiment, the size and/or the shape of the microspots is controlled, e.g. for spatially controlling the location and density of the bioactive compound compositions and for regulating cell behavior.

In a preferred embodiment, the stabilization layer attracts cells to adhere and to onset a local deprotection and leakage (release) of the bioactive compound composition, as e.g. a transfection mixture.

The peptide and/or protein contained in the stabilization layer besides the further polymer is not particularly limited. Preferably, the protein and/or peptide is at least one member selected from the group consisting of fibronectin, laminin, serum albumin, vitronectin, collagen, silk, streptavidin, antibodies, and synthetic peptides, which mimic the above-listed proteins. The above definitions concerning a "biologically active derivative of a protein" analogously apply to such synthetic peptides. Preferably, the stabilization layer comprises a protein-polymer hydrogel, wherein the protein-polymer hydrogel is an extracellular matrix protein-polymer hydrogel, more preferably fibronectin-polymer hydrogel. Most preferably, the stabilization layer consists of a protein-polymer hydrogel, wherein the protein-polymer hydrogel is an extracellular matrix protein-polymer hydrogel, more preferably fibronectin-polymer hydrogel.

The peptide and/or protein used for the peptide-polymer hydrogel may be a natural or synthetic peptide/protein, preferably a natural peptide/protein. For example, human plasma fibronectin or bovine plasma fibronectin can be used for a fibronectin-polymer hydrogel according to the present invention. The peptide/protein may comprise (meth)acrylate groups. The optional (meth)acrylate groups of the peptide/protein may be substituted or unsubstituted. Possible substituents of the optional (meth)acrylate groups of the peptide/protein are selected from the group consisting of amino groups, hydroxyl groups, epoxy groups, alkyl groups, alkenyl groups, alkynyl groups, carboxyl groups, ester groups, and (meth)acrylate groups, aldehydes, cyano groups, ethers, maleimide, thiol groups, azide groups, aryl azides, diazirines, vinyl groups, glycosyl groups, phosphate, dibenzylcyclooctyne, choline, phosphorylcholine, and biotinyl groups, which may also be substituted or unsubstituted.

The polymer contained in the stabilization layer besides the peptide and/or protein is not particularly limited. For example, the polymer may be a biocompatible biostable polymer or a biodisintegrable polymer. Biocompatible biostable polymers may be selected from, but not limited to, at least one of the group consisting of poly(meth)acrylates, polyacrylates, polysiloxanes, polystyrene, vinyl, polyethylene, polypropylene, polycaprolactone and all of the corresponding derivatives. Biodisintegrable polymers may be selected from, but not limited to, at least one of the group consisting of polylactic acid, polyglycolic acid and copolymers and mixtures thereof, such as poly(L-lactide) (PLLA), poly(L,D-lactide), polyglycolic acid (polyglycolode), and poly(L-lactide-co-glycolide), polyamides, polyethylene glycol (PEG), natural polysaccharide (e.g. cellulose, chitin, hyaluronic acid, fatty acid and ester thereof), proteins, and polypeptides (differing from the above-mentioned peptide and/or protein of the protein/peptide layer). Preferably, the polymer comprises at least PEG (a polymer having from 1 to 200 000 ethylene glycol units, preferably 1 to 1000 and most preferably 1 to 10 ethylene glycol units). More preferably, the polymer consists of PEG (a polymer having from 1 to 200 000 ethylene glycol units, preferably 1 to 1000 and most preferably 1 to 10 ethylene glycol units). The polymer may be substituted or unsubstituted. Possible substituents of the polymer are selected from the group consisting of amino groups, hydroxyl groups, epoxy groups, alkyl groups, alkenyl groups, alkynyl groups, carboxyl groups, (meth)acrylate groups, ester groups, and aldehydes, cyano groups, ethers, maleimide, thiol groups, azide groups, aryl azides, diazirines, vinyl groups, glycosyl groups, phosphate, dibenzylcyclooctyne, choline, phosphorylcholine, and biotinyl groups, which may also be substituted or unsubstituted. Most preferably the polymer is PEG (meth)acrylate.

The polymer may be homopolymeric, copolymeric and heteropolymeric (multipolymer interpenetrating polymers, preferably acrylate or methacrylate homopolymeric, copolymeric and (heteropolymeric) multipolymer interpenetrating polymeric hydrogels, and most preferably methacrylate homopolymeric hydrogels.

Preferably, the peptide- and/or the protein-layer is cross-linked with the polymer hydrogel layer. The method for crosslinking the layers is not particularly limited. Thus, any crosslinking method known in the art can be used. For example, crosslinking may be achieved by the use of cross-linking agents like homobifunctional and heterobifunctional reagents, containing two similar or different chemical groups, for example selected from, but not limited to, NHS esters, imidoesters, as e.g. dimethyl suberimidate dihydrochloride (DMS), tetrafluorophenyl ester, maleimide, glutaraldehyde, amines, aldehydes, thiols, alkenyl groups, azides, dibenzocyclooctyne, aryl azides, diazirines, and vinyl groups, and by UV irradiation, e.g. at a wavelength of 254 nm or 360 nm. Moreover, cross-linking may also be achieved with zero length crosslinkers (without any spacer), such as, but not limited to, NHS, EDC (N-(3-Dimethylaminopropyl)-N'-ethylcarbodiimide hydrochloride), DMTMM (4-(4,6-Dimethoxy-1,3,5-triazin-2-yl)-4-methylmorpholinium chloride).

Preferably, cross-linking is achieved by the combination of UV exposure and the addition of a cross-linking agent, preferably DMS. This preferably ensures an excellent physical integrity and physical barrier function of the stabilization layer.

In a preferred embodiment of the present invention, the stabilization layer comprises a protein- and/or peptide-PEG hydrogel. Preferably, the protein- and/or peptide-PEG hydrogel is selected from at least one member of the group consisting of fibronectin-PEG hydrogel, laminin-PEG hydrogel, serum albumin-PEG hydrogel, vitronectin-PEG hydrogel, collagen-PEG hydrogel, silk-PEG hydrogel, streptavidin-PEG hydrogel, antibody-PEG hydrogel, and synthetic peptides, which mimic the above-listed proteins and are crosslinked with PEG hydrogel. More preferably, the stabilization layer comprises a protein-PEG hydrogel selected from at least one member of the group consisting of fibronectin-PEG hydrogel, laminin-PEG hydrogel, serum albumin-PEG hydrogel, vitronectin-PEG hydrogel, collagen-PEG hydrogel, silk-PEG hydrogel, and streptavidin-PEG hydrogel. More preferably, the stabilization layer comprises a protein-PEG hydrogel, wherein the protein-PEG hydrogel is an extracellular matrix protein-PEG hydrogel, more preferably fibronectin-PEG hydrogel. Most preferably, the stabilization layer consists of a protein-PEG hydrogel, wherein the protein-PEG hydrogel is an extracellular matrix protein-PEG hydrogel, more preferably fibronectin-PEG hydrogel. In a preferred embodiment, fibronectin-PEG hydrogels advantageously provide an excellent stabilization to bioactive compound compositions when covering the same. Moreover, fibronectin-PEG hydrogels can adhere cells, are non-toxic, stable in air and water and can be degraded by cells over a certain time period. Preferably, the above materials advantageously combine the property of a biocompatible material (in order to avoid cytotoxicity, genetic toxicity and other negative effects on cells and tissues) and a chemical crosslinkability with excellent physical integrity and physical barrier function.

A protein- and/or peptide-PEG hydrogel according to the present invention comprises at least one protein/peptide layer and at least one layer of a PEG (meth)acrylate hydrogel, which are preferably cross-linked with each other. The protein/peptide used for the peptide-PEG hydrogel may be a natural or synthetic peptide, preferably a natural peptide. For example, human plasma fibronectin or bovine plasma fibronectin can be used for a fibronectin-PEG hydrogel according to the present invention.

PEG (meth)acrylate hydrogels according to the present invention may be produced from one or more PEG (meth) acrylate hydrogel precursors. Examples of PEG (meth) acrylate hydrogel precursors are hydroxyethyl methacrylate (HEMA), polyethylene glycol methacrylate (PEGMA), glycidyl methacrylate, allyl methacrylate, methacrylic acid, and amino ethyl methacrylate (AEMA). In a preferred embodiment, the PEG (meth)acrylate hydrogel according to the present invention is produced from a mixture of hydroxyethyl methacrylate (HEMA), polyethylene glycol methacrylate (PEGMA), and amino ethyl methacrylate (AEMA). Preferably, such a PEG (meth)acrylate hydrogel is very efficient in enclosing the bioactive compound composition.

The stabilization layer may be labelled with a labelling agent, if necessary. Suitable labelling agents are known in the art. For example, labelling agents may include any fluorescent/luminescent compounds or particles like HiLite 488, Texas Red, Cy3, FITC, GFP, and quantum dots, as well as magnetic or plasmonic particles, radioactive labels, etc. Preferably, the labelling agent is HiLite 488. In case the stabilization layer comprises a fibronectin-PEG hydrogel, the stabilization layer can be labelled by labelling the fibronectin component of the fibronectin-PEG hydrogel. Labelled fibronectin can for example be obtained under the name "Fibronectin-HiLyte488 labeled" from Cytoskeleton, Inc.

The stabilization layer may further contain different antibodies, growth factors, chemoattractants, etc.

In a preferred embodiment of the present application, the stabilization layer forms micropatterns. More preferably, the stabilization layer is deposited on the support and the bioactive compound composition as certain geometrical shapes, as e.g. disks, stripes, triangles, and rectangles, with better or less defined borders. The lateral dimensions of the micropatterns range from 0.5 to 50 µm, or from 50 to 500 µm, or from 500 to 10000 µm, or from 500 to 1000 µm. Preferably, by forming such micropatterns, the stabilization layer advantageously possesses cell-adherent properties and is also suitable for further functional modifications, as e.g. covalent or physical attachments of proteins, peptides, other biological molecules, and/or chemical labels.

Preferably, the stabilization layer and/or the bioactive compound compositions is/are bound to the support by non-covalent interactions. Accordingly, no chemically active molecules are preferably used to make patterns on the support. Thus, no chemisorption is preferably used for obtaining the bioactive compound delivery assembly according to the present invention.

In a further aspect, the present invention relates to a method for stabilization and/or encapsulation of bioactive compound compositions, comprising the steps of
(a) disposing at least one bioactive compound composition on a support, and
(b) disposing at least one stabilization layer partially or fully on the at least one bioactive compound composition
wherein the stabilization layer comprises a peptide- and/or protein-polymer hydrogel. The above definitions analogously apply to this aspect of the present invention.

The method for stabilization and/or encapsulation of bioactive compound compositions according to the present invention is based on a stabilization layer, as e.g. a nanometers-thick layer of a fibronectin-PEG hydrogel, which can be applied onto bioactive compound compositions, as e.g. siRNA transfection mixture spots, disposed on a support, as e.g. a glass substrate. Preferably, to maintain a biocompatible and cell-adhesive or cell-repellent environment, the support itself can be modified with e.g. a PEG (meth) acrylate hydrogel with or without different proteins or peptides. As already defined, the stabilization layer preferably comprises a protein- and/or peptide-PEG hydrogel, preferably a fibronectin-hydrogel, in the form of a so-called "nanofoil". A simplified schematic explanation of a preferred embodiment of the production of a protective fibronectin-hydrogel layer for the protection of transfection mixture spots is presented in FIG. 1. First, a double-layer of fibronectin and PEG methacrylate hydrogel precursors, respectively, is formed on a standard polydimethylsiloxane (PDMS) stamp used for microcontact printing. The double layer is then cross-linked to obtain the "nanofoil". The cross-linked nanofoil layer is subsequently stamped on siRNA transfection mixture spots onto standard glass, or e.g. polymer coatings or on other substrates. Due to the microcontact printing process the nanofoil can form micropatterns. Depending on the experimental requirements, the non-covered transfection mixture can be washed out or left on the surface of the support.

The method by which the bioactive compound composition can be disposed on the support in the step (a) is not particularly limited and thus any method known in the art, can be applied. For example, such methods include printing with a pin arrayer, pin/needle deposition, microfluidic/capillary deposition, microcontact printing (µCP), transfer printing, ink-jet printing, aerosol jet printing, dipping, as well as coating techniques, as e.g. spin-coating. If needed, the bioactive compound composition disposed on the support can be additionally structured and/or modified, e.g. by UV exposure, photolithography. Also, the bioactive compound composition can be in situ synthesized on the support. Preferably, the bioactive compound composition is disposed on the support in the step (a) by printing with a pin arrayer.

The method for disposing at least one stabilization layer partially or fully on the at least one bioactive compound in the step (b) is not particularly limited and thus any deposition protocol and tools known in the art can be applied, as e.g. transfer printing, microcontact printing with an elastomeric stamp, roll-to-roll processing. Methods including dispensing with an ink-jet nozzle or a micropipette, evaporating, spraying, dipping and microfluidic deposition, UV and/or other radiation treatments may be used for additional modifications. Examples of automated contact printing include but are not limited to GeSiM and Innopsys microcontact printers. By using this or similar precision instrumentation a better alignment of the stabilization layer with respect to the bioactive compound composition spots/patterns is achieved.

In a preferred embodiment of the present invention, the stabilization layer is disposed on the bioactive compound composition in the step (b) by microcontact printing.

In a preferred embodiment of the present invention, the stabilization layer is formed on a stamp used for the microcontact printing in the step (b) by first forming a double-layer that consists of a protein and/or peptide, preferably fibronectin, and a polymer hydrogel, preferably PEG (meth) acrylate hydrogel, on the stamp and then cross-linking the double-layer for obtaining the stabilization layer. The order of formation of the double-layer is not particularly limited. Preferably, the protein and/or peptide layer and the layer of the polymer hydrogel, preferably PEG (meth)acrylate hydrogel, are disposed in this order on the stamp. The number of protein- and/or peptide-polymer hydrogel double-layers, preferably peptide-PEG (meth)acrylate hydrogel double-layers is not limited to one. Thus, further double-layers may be disposed on previously disposed double-layer(s).

Stamps used for the microcontact printing are not particularly limited and thus any stamp material known in the art can be applied. Preferably, the material of the stamp is chemically inert to serve as a substrate for the synthesis of the stabilization layer of crosslinked PEG hydrogel and proteins/peptides and has elastic properties ensuring a good physical contact with the support, e.g. glass. For example, such stamps include pure polydimethylsiloxane (PDMS) stamps, composite PDMS stamps, agarose stamps, rubber stamps, latex stamps, photopolymer stamps and stamps made of biosynthetic hydrogels with a high Young modulus of at least 50 kPa, preferably at least 150 kPa, and most preferably at least 1 MPa. In the case of clinical applications, the stamp material is preferably GMP-compatible. In a preferred embodiment, the stamp used for microcontact printing is a polydimethylsiloxane (PDMS) stamp. The dimension of the stamp is not particularly limited. For example, the stamp may be square-shaped with dimensions of 10 mm×10 mm. Prior to printing, the stamps may be rinsed in e.g. ethanol, dried e.g. under a stream of nitrogen gas and treated with oxygen plasma (20 W power) e.g. for 30 s in a plasma dry cleaner to render the PDMS surface hydrophilic.

Preferably, the surface topography of the stamp consists of protrusions and depressions having shapes of lines, dots, triangles, squares, and/or any other regular or irregular geometric features with their lateral dimensions ranging from 1 nm to 10000 µm, preferably from 500 nm to 200 µm. The height of the features forming the surface topography is from 1 nm to 1000 µm, more preferably from 1 µm to 50 µm, and most preferably from 5 to 20 µm.

Preferably, a protein and/or peptide layer is formed on the stamp by loading the stamp with an "ink" comprising a protein and/or peptide solution, incubating the "ink" on the stamp, optionally removing excess "ink" and optionally drying the stamp with the applied protein and/or peptide layer. The protein and/or peptide-layer may be optionally cross-linked with a pre-formed polymer hydrogel, preferably PEG (meth)acrylate hydrogel. Such a protein and/or peptide solution comprises the corresponding protein and/or peptide (and the optional cross-linking agents) in appropriate concentrations, e.g. in PBS at pH=8.0. For example, the concentration of the protein and/or peptide may be from 0.001 to 10 mg/mL, preferably from 0.01 to 1.0 mg/mL, more preferably from 0.1 to 0.5 mg/mL and the concentration of the optional cross-linking agent may be from 0.01 to 1 M, preferably from 0.02 to 0.5 M, and more preferably from 0.05 to 0.2 M. The amount of "ink" applied on the stamp is not particularly limited. For example, 30 µl "ink" may be applied to e.g. a 10 mm×10 mm stamp. The incubation time of the "ink" is not particularly limited and may for example be from 1 min to 5 h, preferably from 2 min to 1 h, and more preferably from 5 min to 15 min. The temperature during incubation is not particularly limited and may for example be from 0° C. to 40° C., preferably from 10° C. to 30° C., and more preferably from 20° C. to 25° C. Possible excess "ink" may be removed by rinsing, e.g. with water, for 1 s to 2 h, preferably for 2 s to 30 min, more preferably for 5 s to 3 min, and most preferably for 10 to 30 s. Furthermore, a stamp with the protein and/or peptide layer may be dried e.g. by using a nitrogen gas stream.

Preferably, a polymer hydrogel layer, preferably PEG (meth)acrylate hydrogel layer, is formed on the same stamp by applying another "ink", comprising a polymer hydrogel precursors, preferably PEG (meth)acrylate hydrogel precursors, (and optionally cross-linking agents), to the stamp, polymerizing the polymer hydrogel precursors, preferably PEG (meth)acrylate hydrogel precursors, optionally cross-linking the polymer hydrogel layer, preferably PEG (meth)acrylate hydrogel, with a pre-formed protein and/or peptide layer, optionally removing excess "ink" (after polymerization) and optionally drying the stamp with the formed polymer hydrogel layer, preferably PEG (meth)acrylate hydrogel layer. Such an "ink" comprises the corresponding polymer hydrogel precursor(s), preferably PEG (meth)acrylate hydrogel precursor(s), (and the optional cross-linking agents) in appropriate concentrations, e.g. in PBS at pH=8.0. For example, the total concentration of the polymer hydrogel precursors, preferably PEG (meth)acrylate hydrogel precursor(s), may be from 0.1 to 10 M, preferably from 0.2 to 5 M, and more preferably from 0.5 to 2 M, and the concentration of the optional cross-linking agent may be from 0.01 to 1 M, preferably from 0.02 to 0.5 M, and more preferably from 0.05 to 0.2 M. The amount of "ink" applied on the stamp is not particularly limited. For example, 30 µl "ink" may be applied to e.g. a 10 mm×10 mm stamp. The polymer hydrogel precursors layer, preferably PEG (meth) acrylate hydrogel precursors layer, may be polymerized by any polymerization method known in the art, e.g. by applying UV light (e.g. 254 nm, e.g. 11 W), to form the polymer hydrogel layer, preferably PEG (meth)acrylate hydrogel layer. The UV exposure time is not particularly limited and may for example be from 10 sec to 30 min, preferably from 30 sec to 10 min, and more preferably from 1 min to 5 min. The polymerization may be conducted by using a polymerization catalyst or an initiator. With a catalyst or an initiator hydrogel layers can preferably be formed by using different wavelengths of light, as e.g. 365 nm, or higher temperatures for initiating radicals. In case a peptide layer/PEG (meth) acrylate hydrogel layer has been pre-formed on the stamp and cross-linking agents are included in the "ink" for forming the PEG (meth)acrylate hydrogel layer/peptide layer, the cross-linking agent preferably connects the PEG (meth)acrylate polymer and the peptide layer. The same applies to protein- and/or peptide-polymer hydrogel double-layers. More preferably, the cross-linking reaction occurs simultaneously with the formation of the polymer hydrogel layer, preferably PEG (meth)acrylate hydrogel layer, e.g. upon UV exposure. Possible excess "ink" may be removed by rinsing, e.g. with water, for 1 s to 2 h, preferably for 2 s to 30 min, more preferably for 5 s to 3 min, and most preferably for 10 to 30 s. Furthermore, a stamp with the polymer hydrogel layer, preferably PEG (meth)acrylate hydrogel layer, may be dried e.g. by using a nitrogen gas stream.

The method by which the double-layer of the protein and/or peptide, preferably fibronectin, and the polymer hydrogel precursors, preferably PEG (meth)acrylate hydrogel precursors, can be cross-linked is not particularly limited and thus any method known in the art can be applied. For example, such methods include addition of cross-linking agents, such as homobifunctional and heterobifunctional reagents, containing two similar or different chemical groups, for example selected from, but not limited to, NHS esters, imidoesters, as e.g. dimethyl suberimidate dihydrochloride (DMS), tetrafluorophenyl ester, maleimide, glutaraldehyde, amines, aldehydes, thiols, alkenyl groups, azides, dibenzocyclooctyne, aryl azides, diazirines, and vinyl groups, or with zero length crosslinkers (without any spacer), such as, but not limited to, NHS, EDC (N-(3-Dimethylaminopropyl)-N'-ethylcarbodiimide hydrochloride), DMTMM (4-(4,6-Dimethoxy-1,3,5-triazin-2-yl)-4-methylmorpholinium chloride), to the polymer hydrogel precursors, preferably PEG (meth)acrylate hydrogel precursors, and/or the protein and/or peptide solution used for forming the protein and/or peptide layer. The cross-linking agents may be disposed together with the polymer hydrogel precursors, preferably PEG (meth)acrylate hydrogel precursors, and/or the protein and/or peptide solution used for forming the protein and/or peptide layer. The cross-linking agent may react by itself, e.g. depending on the pH. For example, in case DMS is used as a cross-linking agent, the pH is preferably from 7 to 9. Moreover, the cross-linking may e.g. be started by exposing the double-layer to UV light radiation with or without the presence of a cross-linking agent. For example, by including (meth)acrylate groups in the protein and/or peptide, the protein and/or peptide layer and the polymer hydrogel layer, preferably PEG (meth) acrylate hydrogel layer, may be cross-linked without the presence of cross-linking agents. Preferably, the proteinand/or peptide-polymer hydrogel according to the present invention is cross-linked by the combination of UV exposure and the addition of a cross-linking agent, preferably DMS. This preferably ensures an excellent physical integrity and physical barrier function of the stabilization layer.

The lateral dimensions of the stabilization layer (nanofoil) are not particularly limited. Accordingly, the stabilization layer may fully or partially seal the spot/pattern under it. In case, the bioactive compound composition is small and very soluble, it may be appropriate to dispose a thicker and wider stabilization layer.

In a preferred embodiment of the present invention the method for stabilization and/or encapsulation of bioactive compound compositions further comprises the step of (c) washing for removing the parts of the at least one bioactive compound composition not being covered with the at least one stabilization layer, wherein the step (c) is carried out after the steps (a) and (b).

Preferably, by removing the parts of the at least one bioactive compound composition not being covered with any stabilization layer, it can be ensured that the at least one bioactive compound composition is available only after degrading the at least one stabilization layer. Thus, in a preferred embodiment, when contacting the stabilized and/or encapsulated bioactive compound compositions with cells, it can be ensured that no transfection of the cells with the stabilized and/or encapsulated bioactive compound compositions occurs before the at least one stabilization layer is degraded by the cells.

Preferably, the method for stabilization and/or encapsulation of bioactive compound compositions further comprises the step of (d) disposing at least one further bioactive compound composition on the support, wherein the step (d) is carried out after the steps (a) and (b).

Preferably, the step (d) is carried out after the optional step (c), but may also be carried out in the absence of the step (c). In a preferred embodiment, when disposing at least one further bioactive compound composition, which is not covered by a stabilization layer, besides other fully covered bioactive compound compositions, it is advantageously possible to realize sequential contacting of e.g. cells with the different bioactive compound compositions, as e.g. different transfection mixtures.

In a preferred embodiment the method for stabilization and/or encapsulation of bioactive compound compositions is used for producing the bioactive compound delivery assembly of the present invention.

In a further aspect, the present invention relates to a method for solid-supported transfection of living cells, comprising the steps of (a) providing the bioactive compound delivery assembly according to the present invention, and
(b) providing living cells to the bioactive compound delivery assembly, wherein the bioactive compound composition comprises a transfection mixture. The above definitions analogously apply to this aspect of the present invention.

The method by which the living cells can be provided to the at least one stabilization layer in the step (b) is not particularly limited and thus any method known in the art can be applied. For example, such methods include manual or robotic pipetting, ink-jet or piezzo dispensing, and microfluidic deposition.

In a preferred embodiment of the method for solid-supported transfection of living cells according to the present invention, the transfection mixture is a siRNA transfection mixture.

In a preferred embodiment of the method for solid-supported transfection of living cells according to the present invention, the bioactive compound delivery assembly is provided by the method for stabilization and/or encapsulation of bioactive compound compositions according to the present invention.

In a preferred embodiment, the method for solid-supported transfection of living cells according to the present invention comprises sequential contacting of the cells with different bioactive compound compositions. Preferably, by sequential contacting of the cells with different bioactive compound compositions, as e.g. different transfection mixtures, it is advantageously possible to realize time-resolved effects, as e.g. controlled sequential transfections of the cells.

In a preferred embodiment of the method for solid-supported transfection of living cells according to the present invention, sequential contacting of the cells with different bioactive compound compositions is realized by providing a bioactive compound delivery assembly in step (a), which comprises at least two bioactive compound compositions disposed on the support with at least one bioactive compound composition not being covered by a stabilization layer and with at least one other bioactive compound composition being fully covered with at least one stabilization layer.

In a further aspect, the present invention relates to a use of the bioactive compound delivery assembly according to the present invention for a transfection of living cells and/or for a functional modification of an implant and/or a prosthesis. The above definitions analogously apply to this aspect of the present invention.

In a preferred embodiment, the present invention can be used to functionalize implants, prosthesis, or other biomedical devices, as e.g. contact lenses and catheters. In such applications the desired bioactive substances are applied to the surface of the device and the stabilization/protection (nanofoil) layer is formed. Once the device is inserted in the body, the stabilization layer can start detaching and/or decomposing/degrading and anti-inflammatory, antibiotic, or anti-cancer substances can get released in a controlled fashion (in terms of time and location). The speed of the release and the released dose can be controlled by choosing an optimized composition of the layer. For example, more crosslinked nanofoil can ensure a prolonged release. Also, different ingredients can be used in the synthesis of the stabilization layer, including proteins or peptides that are sensitive to enzymatic or metabolic action.

In a preferred embodiment, the present invention allows not only for the controlled release of bioactive substances from the implants, prosthesis, or other biomedical devices but also can be employed to control healing and tissue regeneration. For example, this can be achieved by realizing specific micropatterns of the protection layer. Cell-adhesive micropatterns, including those made of fibronectin, can be used for cell guidance, controlled differentiation or enhanced cell proliferation. A similar function can be achieved by shaping the stabilization layer, e.g. by using PDMS stamps with different layouts of the surface topographies.

The present invention can be used for the stabilization of bioactive compound compositions, as e.g. cell transfection reagents, printed by e.g. standard TCA (i.e. transfected cell array) fabrication technologies, e.g. pin arraying. For this purpose, a nanometer-thick layer of e.g. PEG MA hydrogel-fibronectin composite can be applied onto the transfection mixture spots. In a preferred embodiment such a nanofoil is readily microcontact printed by employing a PDMS stamp. In a preferred embodiment, the nanofoil itself forms cell-adhesive micropatterns, defined by the surface topography of the PDMS stamp.

Although microcontact printing of larger microfeatures such as of 500 µm-wide continuous stripes typically may need more optimization, in a preferred embodiment the overall quality of the domains of the stabilization layer when microcontact printing the same as 500 µm-wide continuous stripes is excellent over the entire centimeter-sized sample area. The microcontact printing of the stabilization layer does preferably not change the shape of the siRNA spots.

In a preferred embodiment, the removal of the nanofoil-covered transfection mixture spots from the surface started in 3 hours when applying a HeLa cell culture, however, the onset of the material release occurred after 11 or 17 hours from the cell seeding. The nanofoil did not show any signs of toxicity with respect to the HeLa cell culture.

The present invention opens the possibility of true surface-supported, prolonged siRNA transfection technologies in TCA format, over periods of time longer than 48 h. Moreover, it can be applied for controlled drug release and encapsulation, as the nanofoil adhesive properties can be tuned for different bioactive substances and surfaces, respectively.

Additionally, the present invention can be applied for two or more different gene regulations in the same field of view (provided different siRNA is positioned/arrayed in the protected and non-protected zones (i.e. different siRNA is provided with and without the stabilizing layer), a layout that can be fabricated, e.g., by microcontact printing). Thus, time- and space-resolved delivery of transfections mixtures, as e.g. siRNA transfection mixtures, can advantageously be achieved with the present invention. Moreover, functional modifications of the surfaces of implants and prostheses can be realized with the present invention as well.

In a preferred embodiment, the present invention relates to a digital (No/Yes) response type of device, based on wrapping bioactive substances by a nanometer-thick polymeric foil (impermeable at least to cell transfection mixtures), which is rather suddenly removed by adherent cells. In cell culture such a delivery can occur with a delay after seeding the cells. Preferably, the PEG-protein composite crosslinking degree, the thickness of the stabilization layer, and the number (and possibly the type) of adherent cells defines the stability of the stabilization layer and, in turn, the overall amount and rate of the released bioactive compound composition.

Moreover, it is preferably feasible to array spots with different bioactive compounds, especially for in vitro applications, e.g. biochips. The arrayed spots can be turned on individually (one-by-one) by cells adhering also one-by-one.

The figures show:

FIG. 1: Simplified schematic explanation of the fabrication process of a protective fibronectin-hydrogel layer for the protection of transfection mixture spots.

Figure 2:
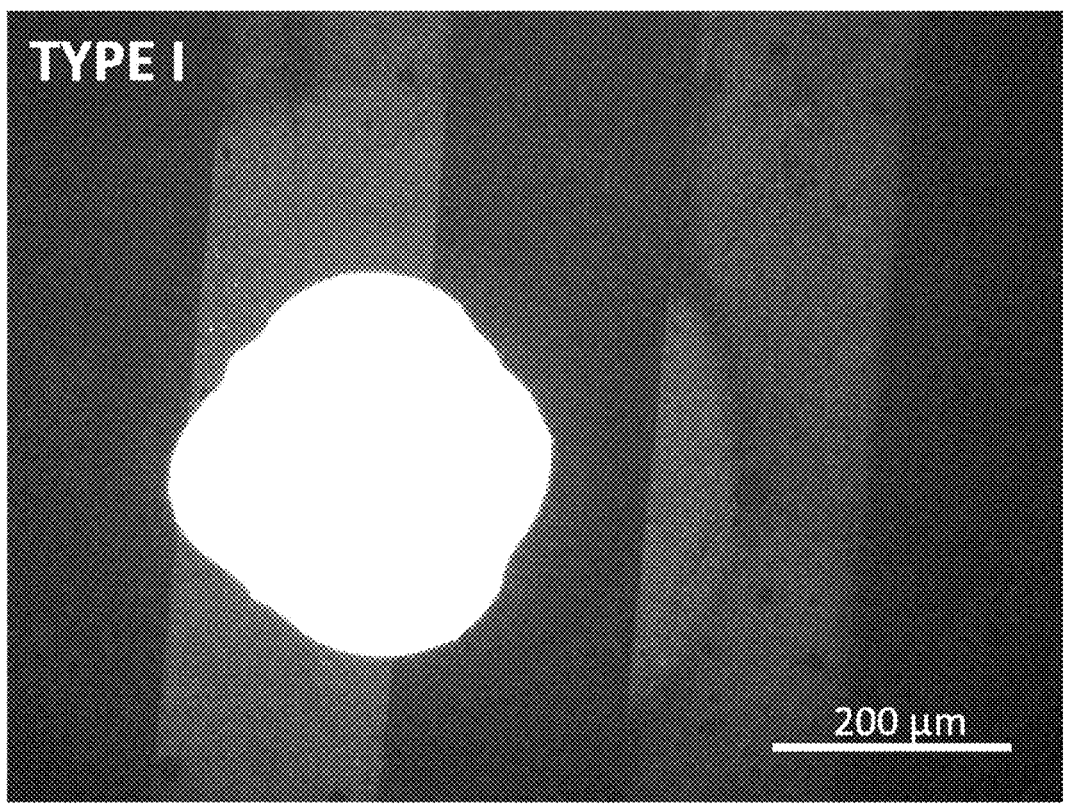
Figure 3:
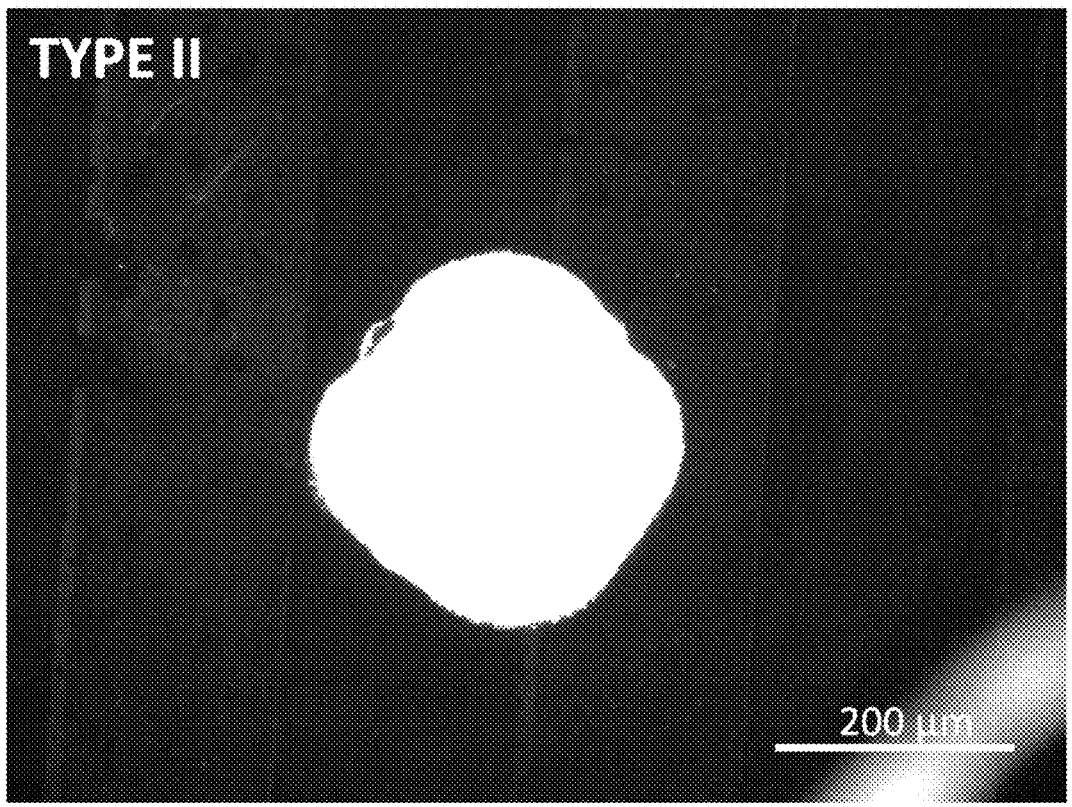

FIGS. 2 and 3: Fluorescence micrographs of model transfection mixture (siRNA-Cy3 and Lipofectamine) spots pin-arrayed on glass/PEG MA hydrogel substrates and covered with 200 µm-wide stripes of the protective nanofoil cover layers. The nanofoil areas are visualized due to the presence of HiLite 488 used for labelling the nanofoils' fibronectin-components. Two preparations of the nanofoil differing in their thickness were tested: Type I (thicker, FIG. 2) and Type II (thinner, FIG. 3), respectively.

Figure 4:
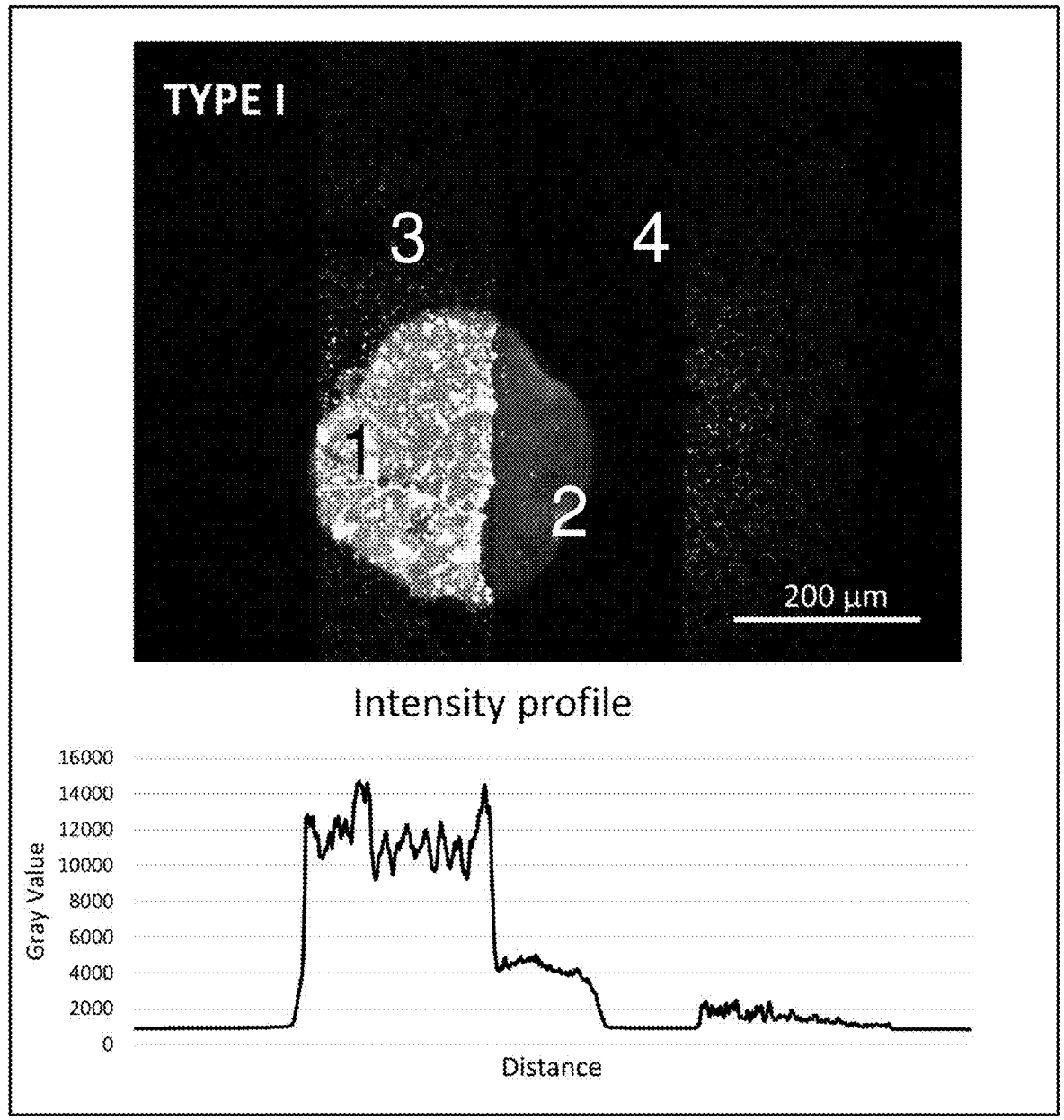
Figure 5:
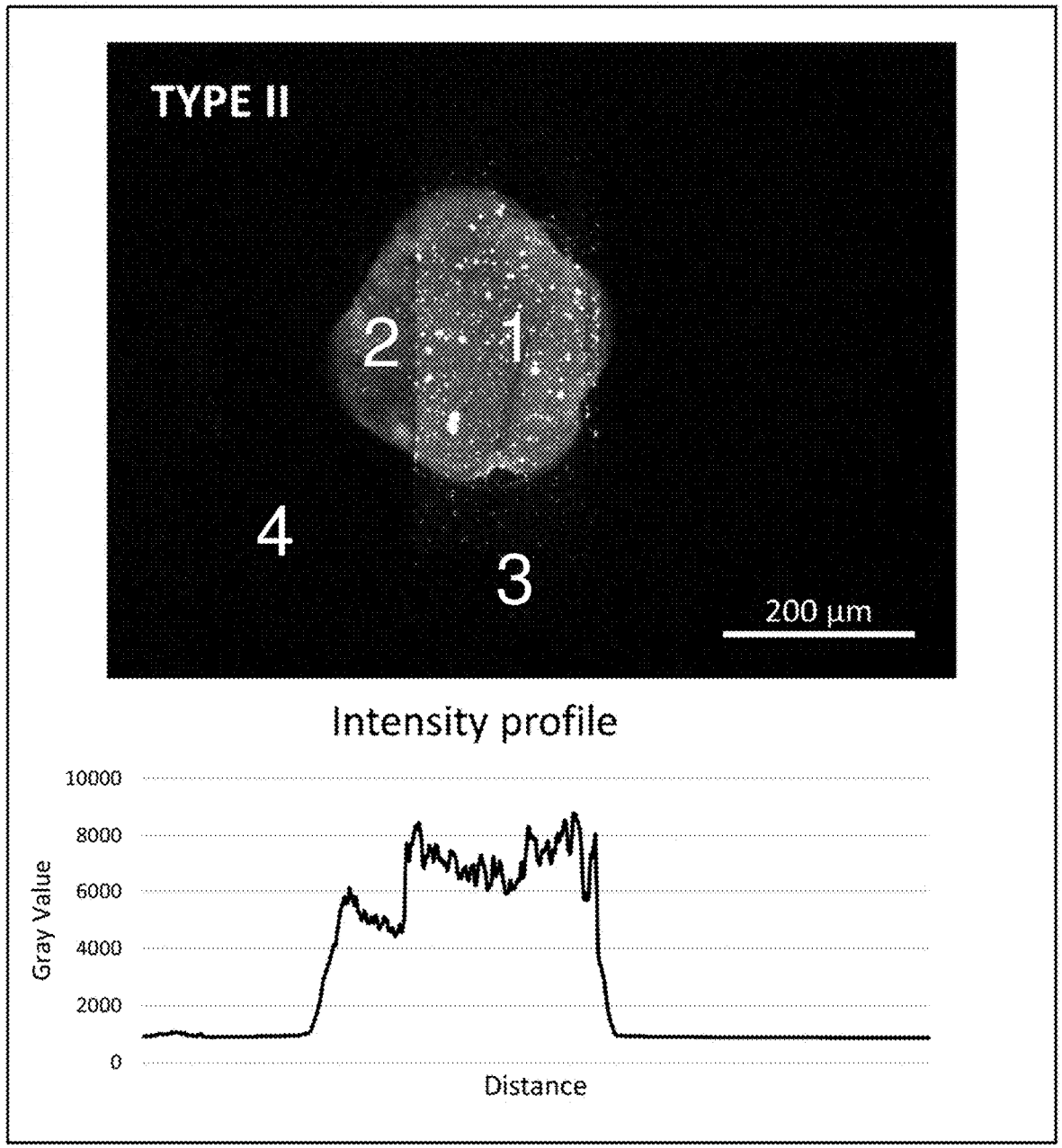

FIGS. 4 and 5: Top: Fluorescence micrographs after the washing of transfection mixture spots covered with two types of nanofoil preparations in buffer (Type I, FIG. 4; Type II, FIG. 5). Bottom: Fluorescence intensity profiles across the micrographs.

Figure 6:
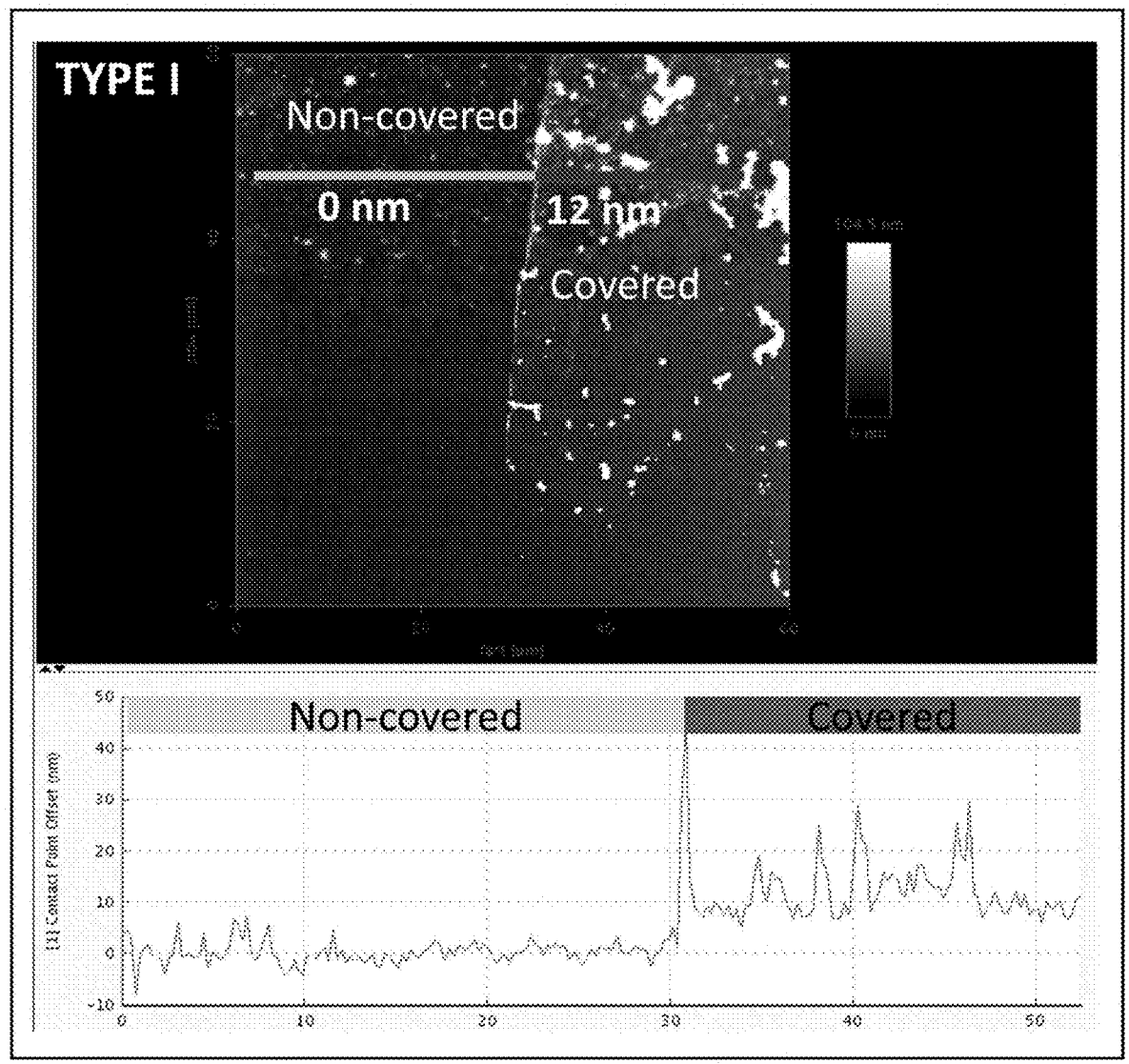
Figure 7:
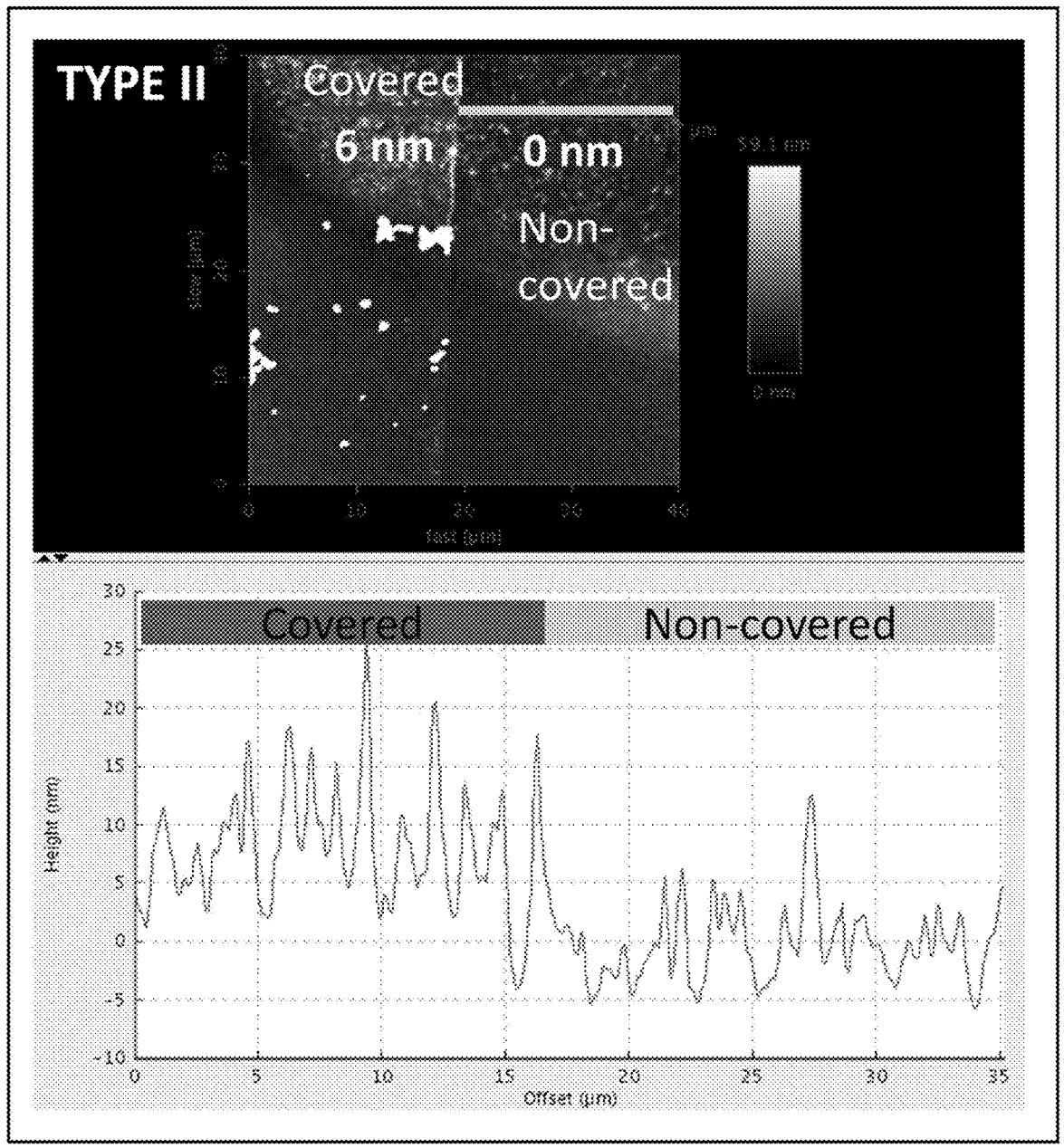

FIGS. 6 and 7: Top: Atomic force microscopy (AFM) topography images after washing of the two types of nanofoil applied onto transfection mixture spots in buffer. Bottom: Height profile analysis of the AFM images along the indicated lines.

Figure 8:
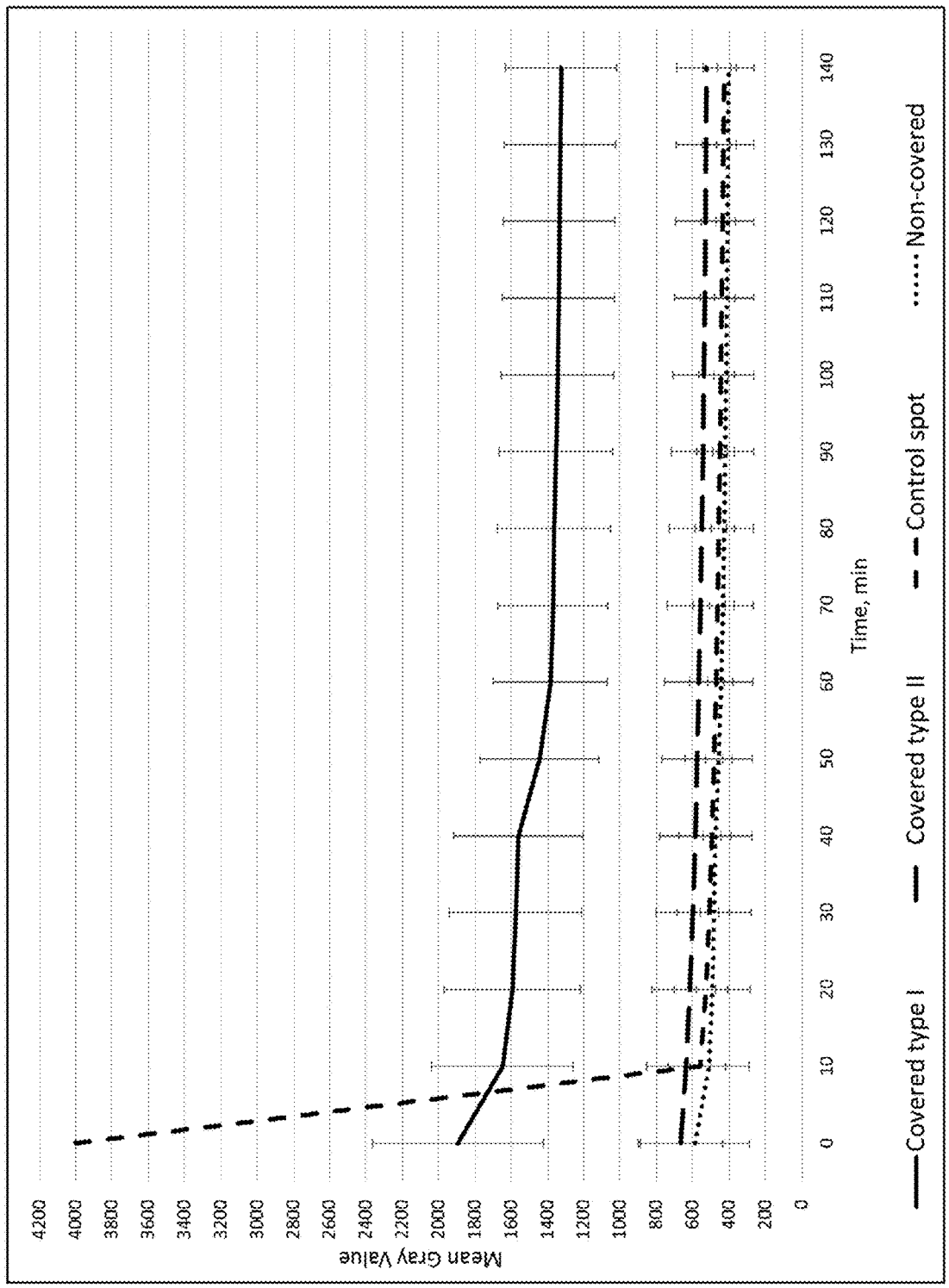
Figure 9:
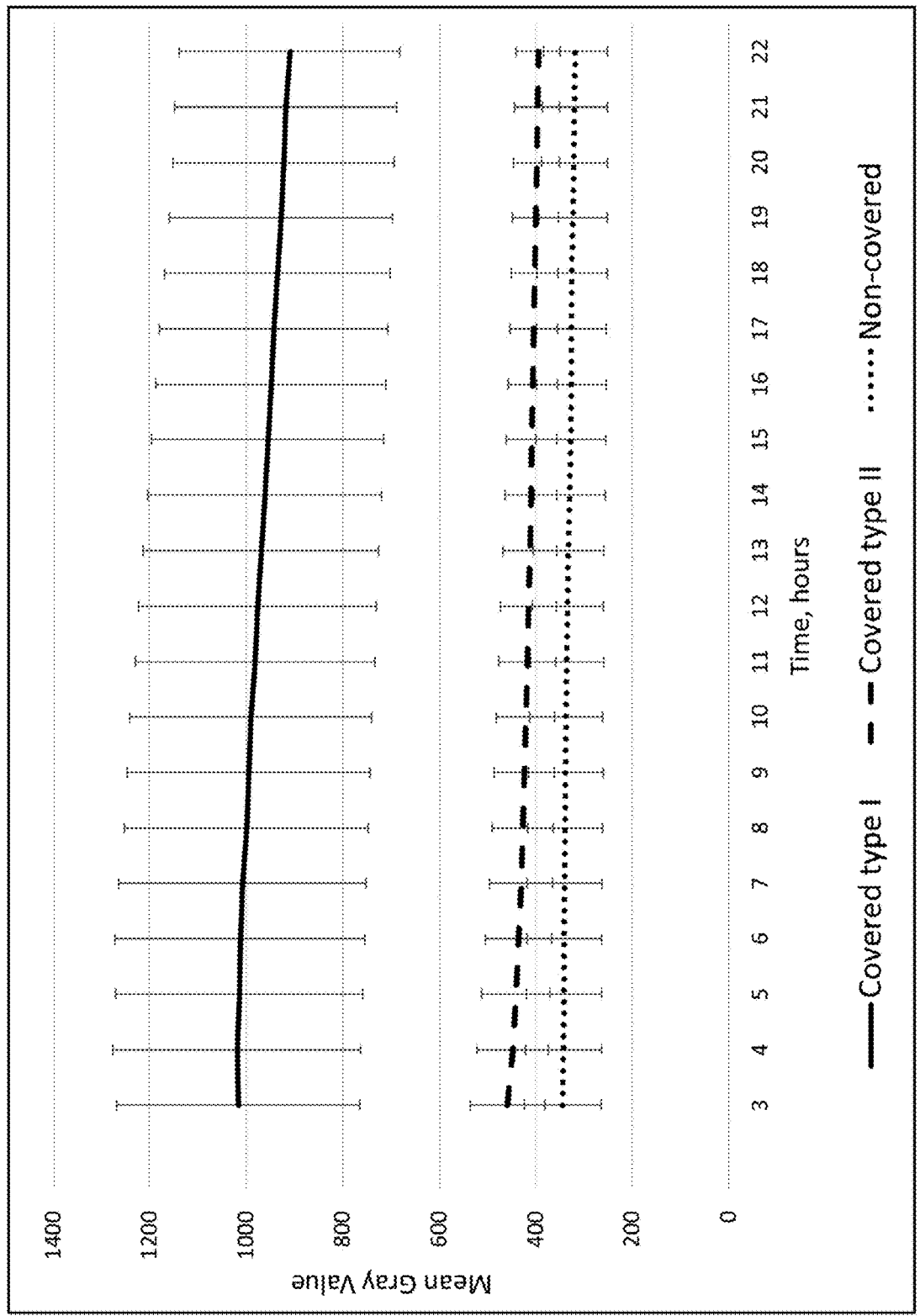

FIGS. 8 and 9: Comparison of fluorescence intensity of siRNA-Cy3 in cell culture: nanofoil Type I (Cover(ed) type I), nanofoil Type II (Cover(ed) type II) and non-covered (non-covered) regions of washed samples. For the first 2.5 h of the experiment the images were taken every 10 min, and in the next 3-23 h the images were taken every 1 h. Several regions of interest of fluorescence microscopy images were analyzed by integrating the total fluorescence (including HeLa cells) in an area of approximately 200×200 µm$^2$. FIG. 8 further shows a control signal (control spot) from a non-washed, non-covered regular TCA sample (control spot, dashed line).

Figure 10:
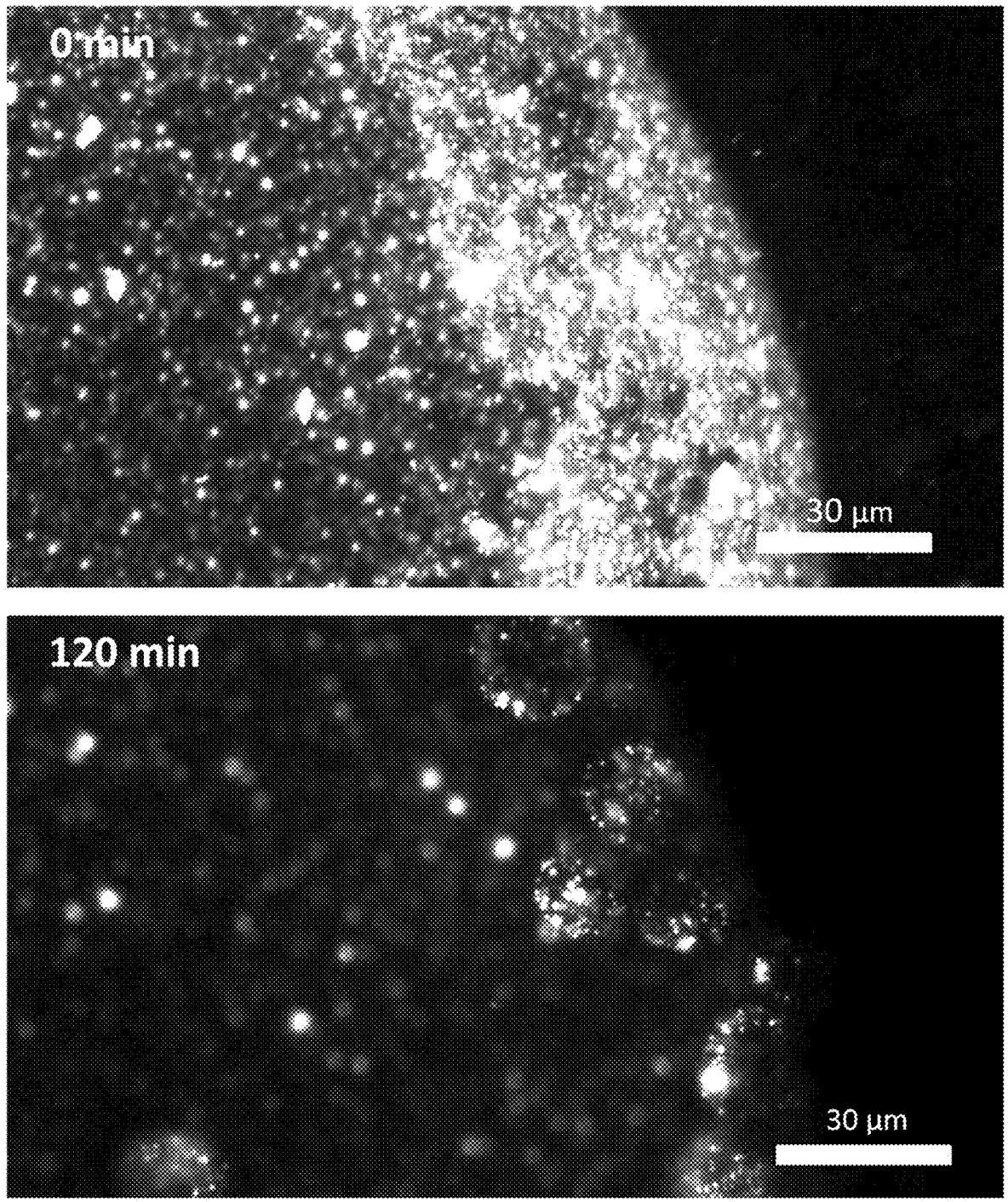

FIG. 10: Fluorescence microscopy images of a non-covered (control) transfection mixture spot, immediately after exposure to HeLa cell culture (top) and after 120 min incubation (bottom).

Figure 11:
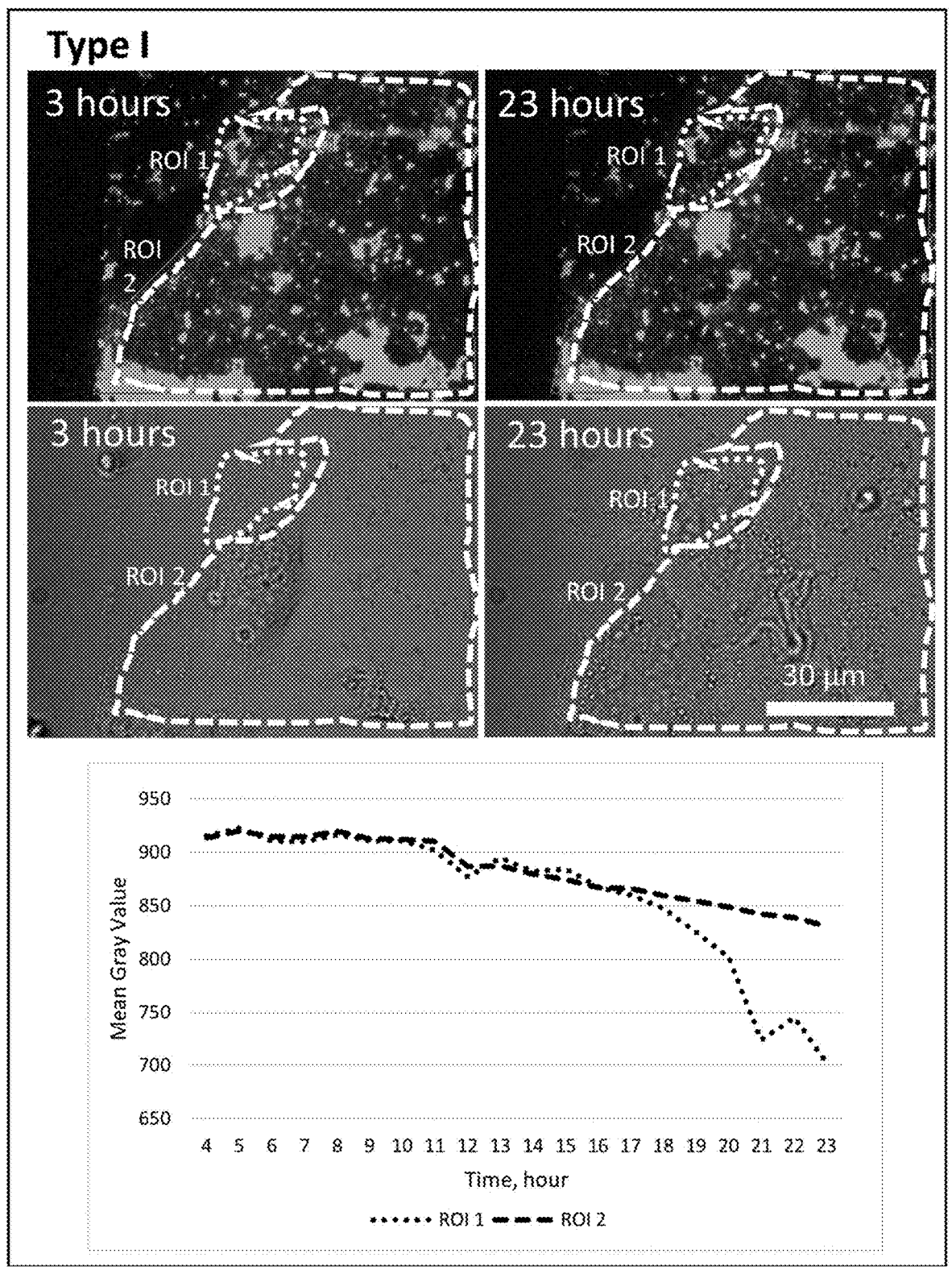
Figure 12:
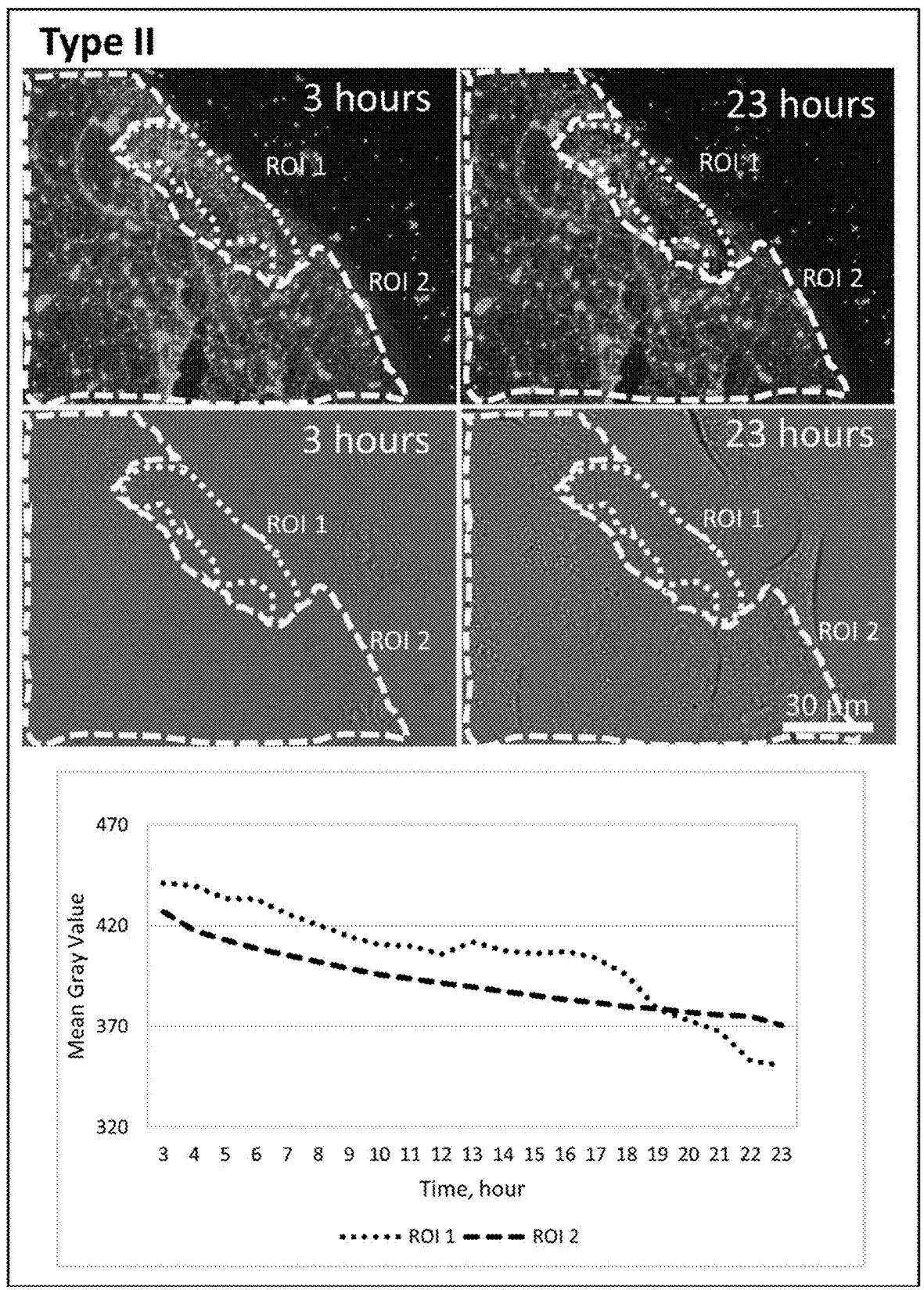

FIGS. 11 and 12: Microscopy monitoring of individual cells adhering to nanofoil-protected siRNA-Cy3 spots (Type I, FIG. 11; Type II, FIG. 12). Top: Fluorescence micrographs. Middle: brightfield microscopy channel. Bottom: Integrated fluorescence signal in the ROIs marked in the micrographs by the different lines. The onset of the transfection mixture release from the surface typically started as initial moving of the material by an "invading" cell, followed by a substantial removal of the material from the ROI.

Figure 13:
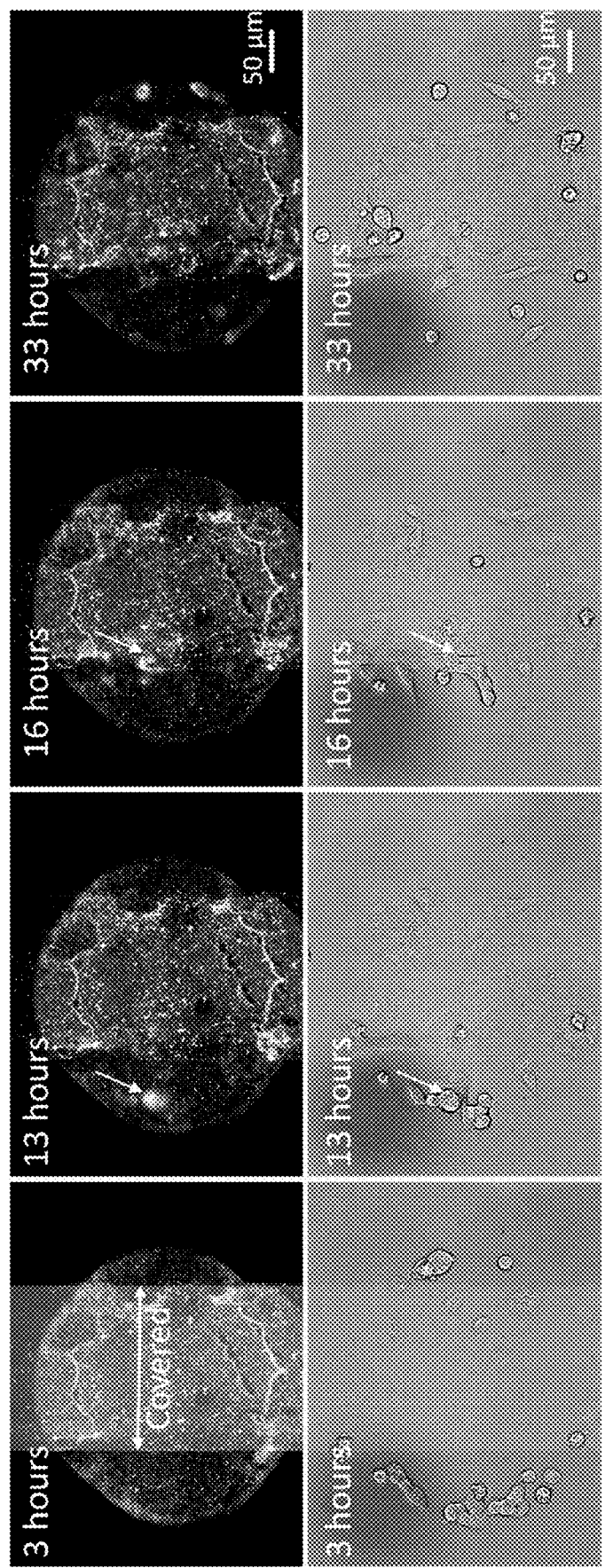

FIG. 13: Microscopy monitoring of HeLa cell interaction with non-covered and nanofoil-covered areas of a siRNA-Cy3 spot, respectively (the position of the nanofoil stripe is indicated in the 3 hours picture). After 3 hours the cells started showing signs of siRNA-Cy3 uptake in non-covered areas of the spot. This process continued until approx. 13 hours, when the number of cells also increased on the nanofoil stripe. The cells accumulated on the rims of the nanofoil stripe at around 16 hours, a process that led to the further degradation of the rims within 33 hours. However, most of the transfection mixture remained stable in the center of the spot for subsequent steps of the controlled release experiment.

Figure 14:
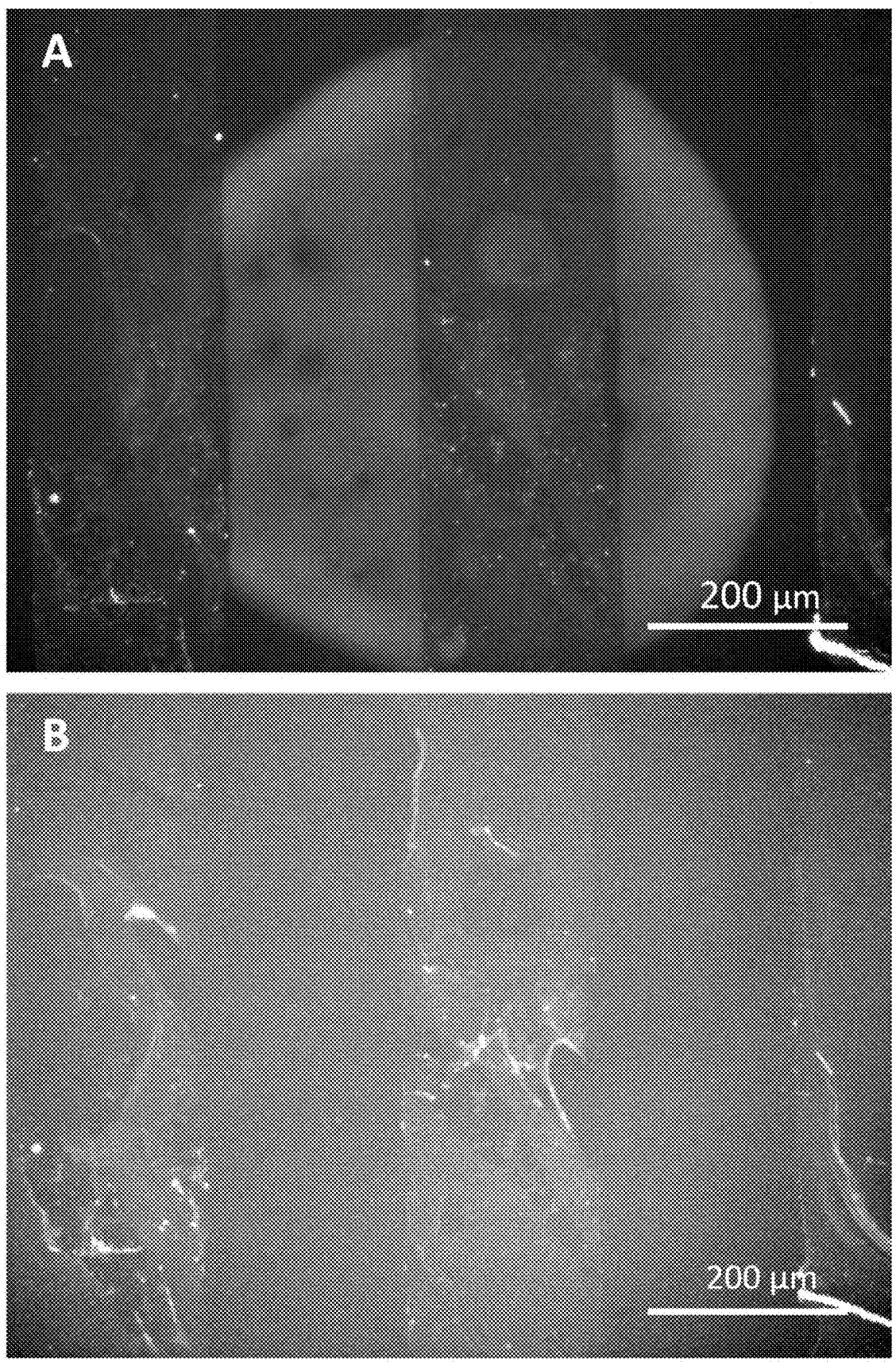

FIG. 14: Fluorescence micrographs of microspots containing a model transfection mixture (siRNA-Cy3 and Lipofectamine) pin-arrayed on glass/PEG MA hydrogel substrates and printed with 200 µm-wide stripe patterns of a composite made from DMS-crosslinked fibronectin and poly-L-lysine layers before (A) and after (B) washing in buffer solution. The composite nanofoil areas are visible due to fluorescence of HiLite 488 used for labelling fibronectin.

Figure 15:
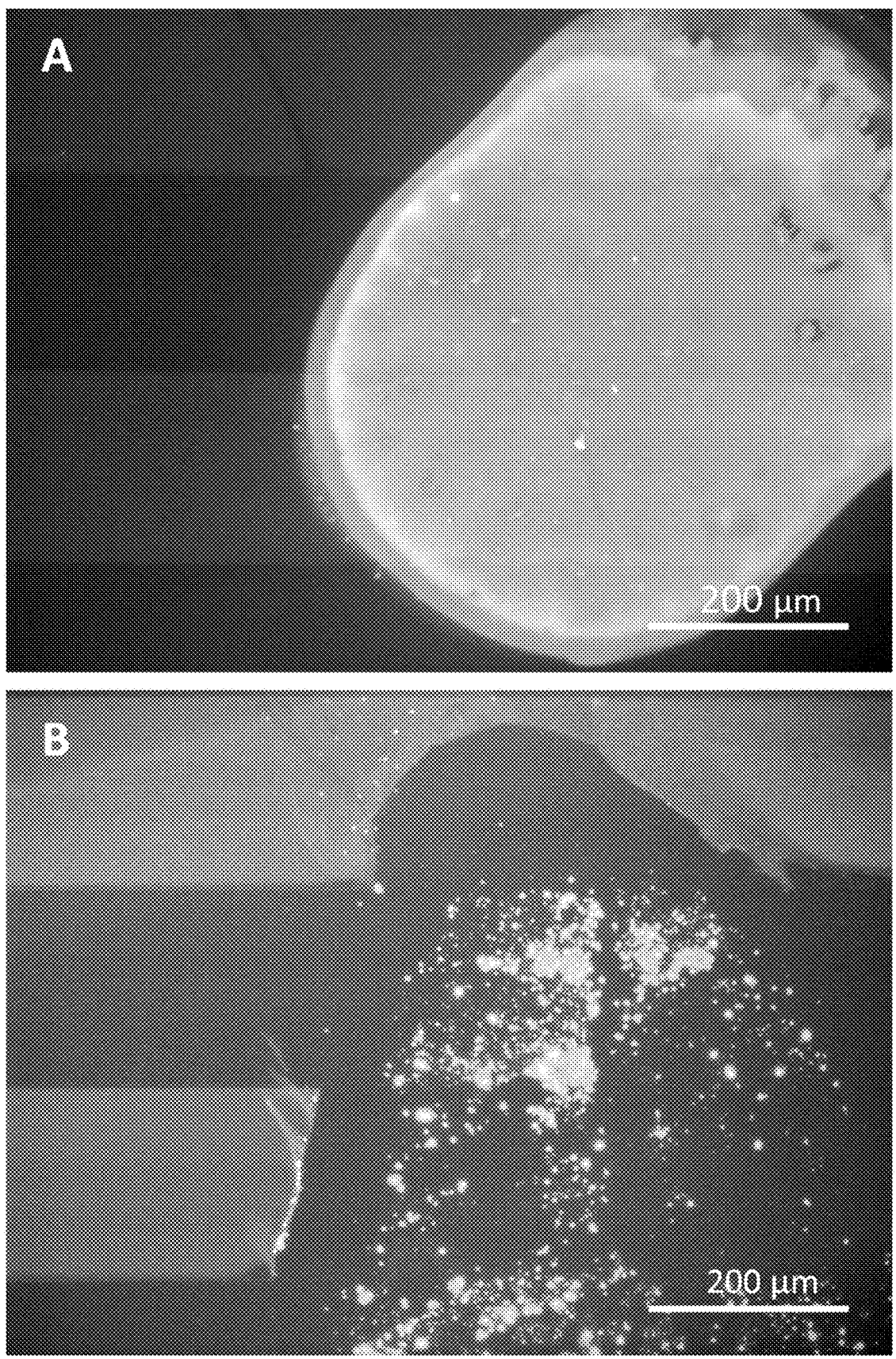

FIG. 15: Fluorescence micrographs of model transfection mixture (siRNA-Cy3 and Lipofectamine) microspots pin-arrayed on glass/PEG MA hydrogel substrates after applying onto them 200 µm-wide stripes of the protective nanofoil stabilization layers of fibronectin and PEGMA hydrogel made without DMS crosslinking. The images were taken before (A) and after (B) the washing procedure. The composite nanofoil areas are visible due to fluorescence of HiLite 488 used for labelling fibronectin.

Figure 16:
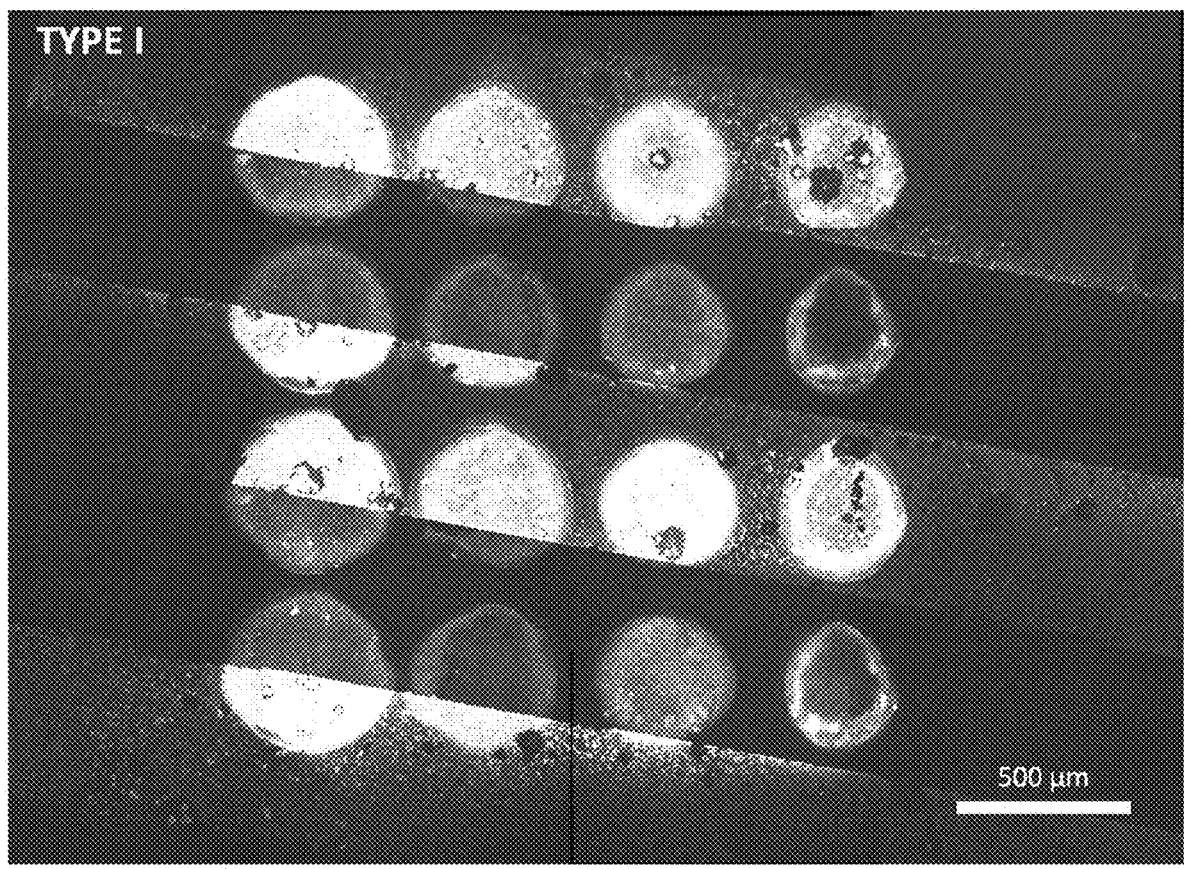

FIG. 16: Overview fluorescence micrograph of an assembly based on a Type I stabilization layer after the washing procedure described in Example 3.

The present invention will be further illustrated in the following examples without being limited thereto.

EXPERIMENTAL PROCEDURES

Automated printing of solid phase transfection mixtures was carried out in different multiwall plates or on glass substrates. Human siRNA microarrays on glass substrates or printed multiwell plates were manufactured and used either for cell culture experiments, or they were further employed as substrates for application of the nanofoil. Automated time-lapse microscopy of human cells transfected on those arrays or multiwell plates and computerized analysis of the phenotypes were carried out by digital image processing software.

Example 1

Square-shaped 10 mm×10 mm poly(dimethylsiloxane) (PDMS) (Dow Corning, Midland, MI, USA) stamps were prepared using a previously published protocol (Zhou Y, Valiokas R, Liedberg B. Langmuir 2004, 20, 6206-6215). To examine the deposition of the fibronectin-PEGMA layer, patterns of 200 µm-wide stripes, separated by 200 µm or 500 µm-wide stripes separated 500 µm were employed. Prior to the printing step, the PDMS stamps were thoroughly rinsed in ethanol, dried under a stream of nitrogen gas and treated with oxygen plasma (20 W power) for 30 s in plasma dry cleaner (Femto, Diener Electronic GmbH, Ebhausen, Germany). The stamps were then loaded with an "ink" comprising a 30 µL solution of 0.1 mg/mL human fibronectin (FN) (Yo Proteins AB, Huddinge, Sweden) mixed with 10 µg/mL bovine plasma fibronectin labeled HiLyte Fluor™ 488 (Cytoskeleton Inc., Denver, CO, USA) in 0.1 M PBS buffer, pH 8.0 for visualization of the patterns. After 10 min. of incubation with "ink" at room temperature, the excess "ink" was removed by water for 20 seconds, than the PDMS stamp was dried using the nitrogen gas stream and another 30 µL "ink" was acquired on a same stamp, containing freshly prepared 240 mM HEMA, 240 mM PEGMA, 360 mM AEMA and 100 mM crosslinking agent DMS (Dimethyl suberimidate dihydrochloride) in PBS pH=8.0. Irradiation of 2 min with UV light (254 nm, 11 W) was used to polymerize the monomers and at the same time letting DMS to connect into polymer in the fibronectin layer. The excess of the second "ink" was removed with water for 20 seconds and dried using nitrogen gas stream.

A glass substrate, collated with a biocompatible PEG methacrylate (PEG MA) hydrogel (obtained from hydroxyethyl methacrylate (HEMA), polyethylene glycol methacrylate (PEGMA), and methacrylic acid (MAA)) (or a glass without coating), with deposited bioactive substance spots (e.g. a transfection mixture) was placed in a Petri dish for preparing the same for microcontact printing (µCP). The surfaces then were printed by applying the PDMS stamp onto the area comprising the bioactive spots. All printing was performed manually without any load, using the nitrogen stream to get the stamp into contact sample. The stamp was left on for five minutes and then removed using tweezers. The printed samples were kept in a dark dry place for future experiments.

Example 2

Model transfection mixture spots of siRNA-Cy3-red/Lipofectamine (Lipofectamine® Transfection Reagent, ThermoFisher) were pin-arrayed on glass slides modified with a biocompatible PEG methacrylate (PEG MA) hydrogel (obtained from hydroxyethyl methacrylate (HEMA), polyethylene glycol methacrylate (PEGMA), and methacrylic acid (MAA)) for a better control of the surface properties. The spots were covered with 200 µm-wide stripes of fibronectin-PEG hydrogel nanofoil layers by microcontact printing (µCP), as for example shown in FIG. 1, in two different thicknesses (thick: Type I, thin: Type II). In the corresponding fluorescence micrographs (FIGS. 2 and 3) the nanofoil appeared as stripes, since a PDMS stamp with a line pattern was employed and since the HiLite 488-labelled fibronectin was used as a component of the nanofoil.

As shown in FIGS. 2 and 3, the nanofoil stripes were efficiently deposited on both the siRNA-containing and unmodified PEG MA areas of the support, respectively. In these experiments it was not intended to fully align the transfection mixture spots and the nanofoil lines.

Example 3

A washing procedure was performed on the transfection mixture spots of Example 2 to evaluate the stability of the nanofoil and of the transfection mixture spots. For this purpose a PBS buffer (phosphate buffered saline; 0.1 M PBD with pH 8.0) was used. After 3 minutes of washing, the samples were taken from the buffer and rinsed carefully in Milli-Q water and dried. The morphology and fluorescence light intensity of the two types of samples was analyzed (FIGS. 4 and 5). As shown in FIGS. 4 and 5, the washing procedure reduced the amount of siRNA when compared to the original spots. However, a substantially larger amount of material stayed under the nanofoil (the areas marked as Region 1 in FIGS. 4 and 5), when compared to the non-covered areas (Region 2 in FIGS. 4 and 5). In this context, the Type I sample exerted a better ability to preserve siRNA. Fluorescence intensity profiles indicated that the siRNA-Cy3 signals in the covered areas of the Type I and Type II samples were about 2.5 and 1.5 times stronger, respectively, when compared to the corresponding non-covered areas.

Example 4

Atomic force microscopy (AFM) was employed to analyze the thickness and morphology of the nanofoil-coated siRNA spots. The AFM topography images (height histograms) of the nanofoil-coated siRNA spots of Example 2 (i.e. before the washing procedure) indicated an about 6 nm higher thickness of the nanofoil-covered transfection mixture spot in the Type I sample when compared to the non-covered transfection mixture spot region, whereas for the Type II sample, this height difference was only about 2 nm. The obtained height values confirmed that the different methods of hydrogel precursor deposition indeed resulted in different thicknesses of the nanofoil.

AFM topography images of the transfection mixture spots of Example 3 (i.e. after washing; FIGS. 6 and 7) indicated a sharp height border between the nanofoil-covered and non-covered areas, respectively, although the transfection material was distributed non-homogeneously. The height difference between the covered and non-covered areas was about 12 nm for the Type I sample and about 6 nm for the Type II sample, respectively.

Example 5

The influence of the nanofoil on the stability of the transfection mixture spots in cell culture was studied. For this purpose, about 60 000 HeLa cells were seeded on each of Type I sample and Type II sample of Example 3 (after washing). The samples were first monitored by fluorescence microscopy for 2.5 h, by recording images every 10 min, and then for up to 23 h, by recording images every 1 h. The results are summarized in FIGS. 8 and 9, by integrating the fluorescence signal in at least 6 different regions of interest (ROIs) on a typical sample (each approximately 200×200 µm$^2$) and representing it as kinetics (nanofoil Type I (Cover (ed) type I), nanofoil Type II (Cover(ed) type II) and non-covered (non-covered) regions of washed samples). Under the same conditions, control samples (control spot) containing no nanofoil on the transfection mixture spots were monitored. As expected, the fluorescence intensity in the control sample went sharply down, suggesting that most of the transfection mixture was washed out by the cell culture media within 10 min. Although a decrease of the integrated fluorescence in the Type I nanofoil sample can be observed within the first hour of monitoring (much less pronounced as for the regular non-covered TCA (i.e. transfected cell array) sample), it levelled out and started to decrease again only after 11 h. For the Type I nanofoil sample only a slow continuous decrease of the signal was observed.

FIG. 10 shows fluorescence microscopy images of a non-covered, control transfection mixture spot (a sample prepared as a regular TCA) and indicates an uptake of siRNA-Cy3 by HeLa cells in a 120 min period.

Example 6

Individual cells adhering to nanofoil-protected siRNA-Cy3 spots of Type I sample and Type II sample of Example 3 (after washing) were monitored by a microscope in several regions of the analyzed samples, thereby observing a delayed uptake of the siRNA-Cy3 from the nanofoil-protected surfaces. FIGS. 11 and 12 show examples of such behavior of HeLa cells on the nanofoil-coated areas of the samples. First signs of transfection mixture removal by the cells can be observed after about 3 h. This process became more obvious after the 11$^{th}$ and 17$^{th}$ hour of the experiment. The onset of the transfection mixture release from the surface started as initial moving of the material by an "invading" cell, followed by a substantial removal of the material from the ROI.

When comparing FIGS. 11 and 12, it can be observed that the controlled release effect in the nanofoil-covered samples is more pronounced for the Type I preparation, most probably since the thicker nanofoil contained more siRNA-Cy3 that could be removed more "abruptly" by the HeLa cells from the surface upon degradation of the stabilization layer.

Example 7

The stability of a transfection mixture upon interaction with cells in different areas of a pin-printed spot that had its central area covered with a nanofoil was monitored (FIG. 13). The cells first concentrated in the non-protected corners of the spot. Said portion of the transfection mixture spot was not washed away completely upon the sample washing procedure and upon the subsequent exposure to the cells, i.e. it likely consisted of relatively stable aggregates formed upon drying after the pin-printing step. The cells internalized significant portions of the non-protected transfection mixture within approx. 13 hours. Then, around 16 hours the cells accumulated around the corners of the nanofoil-protected area and started to degrade the same. Subsequent siRNA release effects were observed in the recorded image frame sequences, between the 13$^{th}$ and 23$^{rd}$ hours of the experiment. However, the central part of the nanofoil zone stayed stable at least for 33 hours, i.e. the major portion of the protected material remained available for causing transfection at later stages of the cell culture experiment. In both types of the nanofoil samples (i.e. Type I and Type II samples of Example 3 (after washing)) there were always sufficient amounts of the transfection mixture under the nanofoil (in the main part of the covered spot) for cell culture experiments that would be longer than 33 hours (FIG. 13).

(Comparative) Example 8

The initial experimental procedures for preparation of the PDMS stamp for the stabilization layer (nanofoil) synthesis were the same as described in Example 1. Subsequently, the PDMS stamp was loaded with 30 µL solution of 0.1 mg/ml human fibronectin (FN) (Yo Proteins AB, Huddinge, Sweden) mixed with 10 µg/ml bovine plasma fibronectin labelled with HiLyte Fluor™ 488 (Cytoskeleton Inc., Denver, CO, USA) in 0.1 M PBS buffer, pH 8.0 for visualization of the formed stabilization layer patterns. After 10 min. of incubation of the PDMS stamp at room temperature, the excess "ink" was removed by immersing in water for 20 seconds, than the PDMS stamp was dried using a nitrogen gas stream. After this step, 30 µL of a different "ink" was added on the same stamp that contained freshly prepared poly-L-lysine (0.1 mg/ml) with 100 mM crosslinking agent DMS (dimethyl suberimidate dihydrochloride). The PDMS stamp was left for 20 min to allow DMS to crosslink fibronectin and poly-L-lysine. The excess of the second "ink" was removed by immersing in water for 20 seconds and the stamp was dried using the nitrogen gas stream. A glass slide coated with PEGMA hydrogel (or a glass slide without coating) was used as a substrate for arraying bioactive substance spots (e.g. a siRNA-containing transfection mixture). The glass substrate comprising the bioactive microspots was placed in a Petri dish. The glass surface was then printed by applying the PDMS stamp with the synthesized cover layer onto the area comprising the bioactive microspots. All printing was performed manually without any load, using the nitrogen stream to bring the PDMS stamp into contact with the sample. The stamp was left on the glass slide for five minutes and then removed using tweezers. The printed samples were kept in a dark dry place for further experiments. FIG. 14 shows the fabricated bioactive compound delivery assembly before and after a washing procedure as described in Example 3. Although the stabilization layer consisting of fibronectin and poly-L-lysine was successfully transferred onto the bioactive microspots, it did not prevent the bioactive microspots from dissolving in buffered solution. Thus, the stabilization layer with poly-L-lysine being simply used as a replacement instead of a PEG hydrogel is not able to provide a suitable stabilization of the bioactive compound-containing microspots.

(Comparative) Example 9

The experimental procedures for preparation of the PDMS stamp and for the synthesis of the composite cover layer on it were the same as described in Example 1, except that no crosslinking agent DMS was used. The substrates with the bioactive compound microspots and the stabilization layer application procedure were the same as in Example 1. FIG. 15 shows the fabricated bioactive compound delivery assembly before and after a washing procedure as described in Example 3. The stabilization layer of fibronectin and PEGMA synthesized without using DMS was successfully transferred onto the bioactive compound microspots. After the washing step in PBS buffered solution the composite layer sections on the microspots decompose and are washed away together with the bioactive compound from the surface.

The invention claimed is:

1. A bioactive compound delivery assembly, comprising
a support,
at least one bioactive compound composition disposed in non-contiguous spots on the support, each spot of the non-contiguous spots has borders forming a discontinuous layer of the at least one bioactive compound composition, and each spot of the non-contiguous spots has a dimension ranging from 1 nm to 1000 µm, and
a stabilization layer partially or fully covering the spots of the at least one bioactive compound composition,
wherein the stabilization layer comprises a peptide- and/or protein-polymer hydrogel, wherein a peptide- and/or protein-layer is crosslinked with a polymer hydrogel layer, wherein the stabilization layer has a thickness in the range of 0.1 to 100 nm, and wherein at least one lateral dimension of the stabilization layer is in the range of 1 to 10,000 µm.

2. The bioactive compound delivery assembly according to claim 1, wherein the support comprises at least one member selected from the group consisting of glass, semiconductor, metal, silicon, polymer-substrate, polymer coating, bioplastics, elastomers, ceramics, living tissue, implant, prosthesis, medical devices, and insoluble polymer material.

3. The bioactive compound delivery assembly according to claim 1, wherein a surface of the support, on which the bioactive compound composition is disposed, is modified with at least one member selected from the group consisting of collagen, fibronectin, laminin, peptides, lipids, Gamma Amino Propyl Silane (GAPS), other silanes, mono- or multifunctional organic compounds, sucrose, polyethylene glycol, polyethylene glycol based hydrogels, polylysine, hyaluronic acid, and Matrigel.

4. The bioactive compound delivery assembly according to claim 1, wherein the bioactive compound composition comprises a cell transfection mixture.

5. The bioactive compound delivery assembly according to claim 1, wherein the peptide- and/or protein-polymer hydrogel is a peptide- and/or protein-PEG hydrogel selected from at least one member of the group consisting of fibronectin-PEG hydrogel, laminin-PEG hydrogel, serum albumin-PEG hydrogel, vitronectin-PEG hydrogel, collagen-PEG hydrogel, silk-PEG hydrogel, streptavidin-PEG hydrogel, antibody-PEG hydrogel, and synthetic peptides, which mimic the above-listed proteins and are crosslinked with PEG hydrogel.

6. The bioactive compound delivery assembly according to claim 1, wherein the stabilization layer comprises micropatterns.

7. The bioactive compound delivery assembly according to claim 1, wherein the bioactive compound delivery assembly comprises at least two bioactive compound compositions disposed on the support with at least one bioactive compound composition not being covered by a stabilization layer and with at least one other bioactive compound composition being fully covered with at least one stabilization layer.

8. A method for stabilization and/or encapsulation of bioactive compound compositions, comprising the steps of
(a) disposing at least one bioactive compound composition in non-contiguous spots on a support, each spot of the non-contiguous spots has borders forming a discontinuous layer of the at least one bioactive compound composition, and each spot of the non-contiguous spots has a dimension ranging from 1 nm to 1000 µm, and
(b) disposing a stabilization layer partially or fully on the spots of the at least one bioactive compound composition,
wherein the stabilization layer comprises a peptide- and/or protein-polymer hydrogel, wherein a peptide- and/or protein-layer is crosslinked with a polymer hydrogel layer, wherein the stabilization layer has a thickness in the range of 0.1 to 100 nm, and wherein at least one lateral dimension of the stabilization layer is in the range of 1 to 10,000 µm.

9. The method according to claim 8, wherein the support comprises at least one member selected from the group consisting of glass, semiconductor, metal, silicon, polymer-substrate, polymer coating, bioplastics, elastomers, ceramics, living tissue, implant, prosthesis, medical devices, and insoluble polymer material.

10. The method according to claim 8, wherein a surface of the support, on which the bioactive compound composition is disposed, is modified with at least one member selected from the group consisting of collagen, fibronectin, laminin, peptides, lipids, Gamma Amino Propyl Silane (GAPS), other silanes, mono- or multifunctional organic compounds, sucrose, polyethylene glycol, polyethylene glycol based hydrogels, polylysine, hyaluronic acid, and Matrigel.

11. The method according to claim 8, wherein the bioactive compound composition comprises a cell transfection mixture.

12. The method according to claim 8, wherein the peptide- and/or protein-polymer hydrogel is a peptide- and/or protein-PEG hydrogel selected from at least one member of the group consisting of fibronectin-PEG hydrogel, laminin-PEG hydrogel, serum albumin-PEG hydrogel, vitronectin-PEG hydrogel, collagen-PEG hydrogel, silk-PEG hydrogel, streptavidin-PEG hydrogel, antibody-PEG hydrogel, and synthetic peptides, which mimic the above-listed proteins and are crosslinked with PEG hydrogel.

13. The method according to claim 8, wherein the stabilization layer comprises micropatterns.

\* \* \* \* \*